(12) United States Patent
Klun et al.

(10) Patent No.: US 10,011,735 B2
(45) Date of Patent: Jul. 3, 2018

(54) DIURETHANE (METH)ACRYLATE-SILANE COMPOSITIONS AND ARTICLES INCLUDING THE SAME

(71) Applicant: 3M INNOVATIVE PROPERTIES COMPANY, St. Paul, MN (US)

(72) Inventors: Thomas P. Klun, Lakeland, MN (US); Alan K. Nachtigal, Minneapolis, MN (US); Joseph C. Spagnola, Woodbury, MN (US); Mark A. Roehrig, Stillwater, MN (US); Jennifer K. Schnobrich, St. Paul, MN (US); Guy D. Joly, Shoreview, MN (US); Christopher S. Lyons, St. Paul, MN (US)

(73) Assignee: 3M INNOVATIVE PROPERTIES COMPANIES, St. Paul, MN (US)

( * ) Notice: Subject to any disclaimer, the term of this patent is extended or adjusted under 35 U.S.C. 154(b) by 529 days.

(21) Appl. No.: 14/419,324

(22) PCT Filed: Mar. 1, 2013

(86) PCT No.: PCT/US2013/028508
§ 371 (c)(1),
(2) Date: Feb. 3, 2015

(87) PCT Pub. No.: WO2014/025385
PCT Pub. Date: Feb. 13, 2014

(65) Prior Publication Data
US 2015/0344504 A1 Dec. 3, 2015

Related U.S. Application Data

(60) Provisional application No. 61/681,008, filed on Aug. 8, 2012, provisional application No. 61/681,003, filed
(Continued)

(51) Int. Cl.
*H01L 51/00* (2006.01)
*C09D 143/04* (2006.01)
(Continued)

(52) U.S. Cl.
CPC ............. *C09D 143/04* (2013.01); *B05D 1/60* (2013.01); *B05D 3/067* (2013.01); *B05D 3/068* (2013.01);
(Continued)

(58) Field of Classification Search
CPC .. C09D 143/04; C09D 133/14; C09D 135/02; B05D 1/60; B05D 3/067; C08K 3/34;
(Continued)

(56) References Cited

U.S. PATENT DOCUMENTS

| 3,600,216 A | 8/1971 | Stewart |
| 4,378,250 A | 3/1983 | Treadway |

(Continued)

FOREIGN PATENT DOCUMENTS

| CN | 1154087 A | 7/1997 |
| CN | 1771127 A | 5/2006 |

(Continued)

OTHER PUBLICATIONS

Affinito, "Polymer-Oxide Transparent Barrier Layers", Society of Vacuum Coaters 39th Annual Technical Conference Proceedings, 1996, pp. 392-397.
(Continued)

*Primary Examiner* — Ruiyun Zhang
(74) *Attorney, Agent, or Firm* — James A. Baker

(57) ABSTRACT

Diurethane (meth)acrylate-silane precursor compounds prepared by reacting a primary or secondary aminosilane with a cyclic carbonate to yield a hydroxylalkylene-carbamoylalkylene-alkoxysilanes (referred to as a "hydroxylcarbamoylsilane"), which is reacted with a (meth)acrylated material
(Continued)

having isocyanate functionality, either neat or in solvent, and optionally with a catalyst, such as a tin compound. Also described are articles including a substrate, a base (co) polymer layer on a major surface of the substrate, an oxide layer on the base (co)polymer layer; and a protective (co) polymer layer on the oxide layer, the protective (co)polymer layer including the reaction product of at least one diurethane (meth)acrylate-silane precursor compound. The substrate may be a (co)polymer film or an electronic device such as an organic light emitting device, electrophoretic light emitting device, liquid crystal display, thin film transistor, or combination thereof. Methods of making the diurethane (meth)acrylate-silane and their use in composite films and electronic devices are described.

20 Claims, 1 Drawing Sheet

Related U.S. Application Data on Aug. 8, 2012, provisional application No. 61/681,023, filed on Aug. 8, 2012, provisional application No. 61/681,051, filed on Aug. 8, 2012, provisional application No. 61/680,995, filed on Aug. 8, 2012.

(51) Int. Cl.

| | | |
|---|---|---|
| *C07F 7/18* | (2006.01) | |
| *H01L 51/52* | (2006.01) | |
| *H01L 51/44* | (2006.01) | |
| *H01L 51/10* | (2006.01) | |
| *B05D 3/06* | (2006.01) | |
| *B32B 27/30* | (2006.01) | |
| *C08J 7/04* | (2006.01) | |
| *C09D 133/14* | (2006.01) | |
| *B05D 1/00* | (2006.01) | |
| *B05D 3/10* | (2006.01) | |
| *C08K 3/34* | (2006.01) | |
| *C09D 135/02* | (2006.01) | |
| *C23C 14/08* | (2006.01) | |
| *C23C 14/34* | (2006.01) | |
| *C23C 16/40* | (2006.01) | |
| *C23C 16/44* | (2006.01) | |
| *C08F 130/08* | (2006.01) | |
| *C09J 133/14* | (2006.01) | |

(52) U.S. Cl.
CPC ............ *B05D 3/101* (2013.01); *B32B 27/308* (2013.01); *C07F 7/1868* (2013.01); *C08F 130/08* (2013.01); *C08J 7/045* (2013.01); *C08K 3/34* (2013.01); *C09D 133/14* (2013.01); *C09D 135/02* (2013.01); *C09J 133/14* (2013.01); *C23C 14/08* (2013.01); *C23C 14/34* (2013.01); *C23C 16/40* (2013.01); *C23C 16/44* (2013.01); *H01L 51/004* (2013.01); *H01L 51/107* (2013.01); *H01L 51/448* (2013.01); *H01L 51/5253* (2013.01); *B32B 2250/04* (2013.01); *B32B 2307/7242* (2013.01); *B32B 2307/7244* (2013.01); *C08J 2333/12* (2013.01); *Y10T 428/1064* (2015.01); *Y10T 428/31507* (2015.04); *Y10T 428/31551* (2015.04); *Y10T 428/31609* (2015.04); *Y10T 428/31663* (2015.04)

(58) Field of Classification Search
CPC ........ B32B 327/308; B32B 2703/7242; B32B 2703/7244; C07F 7/1868; C08F 130/08; H01L 51/004; H01L 51/107; H01L 51/448; H01L 51/5253; Y10T 428/1064
USPC .......... 428/1.51, 447, 429; 427/255.18, 162, 427/164, 167, 387; 556/400, 419
See application file for complete search history.

(56) References Cited

U.S. PATENT DOCUMENTS

| | | |
|---|---|---|
| 4,650,889 A | 3/1987 | Plueddemann |
| 4,696,719 A | 9/1987 | Bischoff |
| 4,722,515 A | 2/1988 | Ham |
| 4,842,893 A | 6/1989 | Yializis |
| 4,889,768 A | 12/1989 | Yokoshima |
| 4,954,371 A | 9/1990 | Yializis |
| 4,983,737 A | 1/1991 | Ravichandran |
| 5,018,048 A | 5/1991 | Shaw |
| 5,032,461 A | 7/1991 | Shaw |
| 5,097,800 A | 3/1992 | Shaw |
| 5,125,138 A | 6/1992 | Shaw |
| 5,142,012 A | 8/1992 | Furukawa |
| 5,233,006 A | 8/1993 | Wolter |
| 5,384,342 A | 1/1995 | Szum |
| 5,399,738 A | 3/1995 | Wolter |
| 5,440,446 A | 8/1995 | Shaw |
| 5,442,071 A | 8/1995 | Galbo |
| 5,532,398 A | 7/1996 | Wolter |
| 5,547,908 A | 8/1996 | Furuzawa |
| 5,654,084 A | 8/1997 | Egert |
| 5,696,179 A | 12/1997 | Chawla |
| 5,770,301 A | 6/1998 | Murai |
| 5,866,651 A | 2/1999 | Moren |
| 5,877,895 A | 3/1999 | Shaw |
| 5,888,491 A | 3/1999 | Mitra et al. |
| 5,891,958 A | 4/1999 | Nambu |
| 6,010,751 A | 1/2000 | Shaw |
| 6,045,864 A | 4/2000 | Lyons |
| 6,169,140 B1 | 1/2001 | Roesler et al. |
| 6,214,422 B1 | 4/2001 | Yializis |
| 6,231,939 B1 | 5/2001 | Shaw |
| 6,335,479 B1 | 1/2002 | Yamada |
| 6,358,863 B1 | 3/2002 | Desu |
| 6,413,645 B1 | 7/2002 | Graff |
| 6,522,067 B1 | 2/2003 | Graff |
| 6,531,560 B1 | 3/2003 | Campbell |
| 6,548,912 B1 | 4/2003 | Graff |
| 6,573,652 B1 | 6/2003 | Graff |
| 6,815,043 B2 | 11/2004 | Fleming |
| 6,835,950 B2 | 12/2004 | Brown |
| 6,852,393 B2 | 2/2005 | Gandon |
| 6,866,901 B2 | 3/2005 | Burrows |
| 7,018,713 B2 | 3/2006 | Padiyath |
| 7,943,062 B2 | 5/2011 | Swager |
| 8,129,205 B2 | 3/2012 | Rana |
| 8,193,698 B2 | 6/2012 | Klein |
| 8,221,176 B2 | 7/2012 | Yoo |
| 8,399,102 B2 | 3/2013 | Oertli |
| 2003/0049995 A1 | 3/2003 | Schutz |
| 2003/0203210 A1 | 10/2003 | Graff |
| 2004/0032658 A1 | 2/2004 | Fleming |
| 2004/0115445 A1 | 6/2004 | Sasaki et al. |
| 2004/0195967 A1 | 10/2004 | Padiyath et al. |
| 2004/0265602 A1 | 12/2004 | Kobayashi |
| 2005/0047740 A1 | 3/2005 | Gantt |
| 2006/0057398 A1 | 3/2006 | Zimmermann |
| 2007/0020451 A1 | 1/2007 | Padiyath |
| 2007/0135572 A1 | 6/2007 | Wolter |
| 2007/0185270 A1 | 8/2007 | Arndt |
| 2007/0286993 A1 | 12/2007 | Radcliffe |
| 2008/0196664 A1 | 8/2008 | David |
| 2009/0208719 A1 | 8/2009 | Kang |
| 2009/0214879 A1 | 8/2009 | Jucker |
| 2010/0039028 A1 | 2/2010 | Suzuki |
| 2010/0210862 A1 | 8/2010 | Tsuchida et al. |
| 2011/0081502 A1 | 4/2011 | Bright |
| 2011/0223434 A1 | 9/2011 | Roehrig |

(56) References Cited

U.S. PATENT DOCUMENTS

| | | |
|---|---|---|
| 2012/0003448 A1 | 1/2012 | Weigel |
| 2012/0003451 A1 | 1/2012 | Weigel |
| 2012/0003484 A1 | 1/2012 | Roehrig et al. |
| 2012/0160402 A1 | 6/2012 | Ho |
| 2012/0164434 A1 | 6/2012 | Ramadas |
| 2012/0301634 A1 | 11/2012 | Nakamura |
| 2012/0301635 A1 | 11/2012 | Hasegawa |
| 2013/0164546 A1 | 6/2013 | Oertli |
| 2013/0260144 A1 | 10/2013 | Yamazaki |
| 2013/0323519 A1 | 12/2013 | Klun |
| 2015/0203707 A1 | 7/2015 | Klun |

FOREIGN PATENT DOCUMENTS

| | | |
|---|---|---|
| CN | 101522417 A | 2/2009 |
| CN | 102458852 A | 5/2012 |
| EP | 2186866 A | 5/2010 |
| EP | 2529926 A | 12/2012 |
| JP | 1-110572 | 4/1989 |
| JP | H01-304108 A | 12/1989 |
| JP | 2-130139 | 5/1990 |
| JP | H02-133338 A | 5/1990 |
| JP | H08-512256 A | 12/1996 |
| JP | H11-503937 A | 4/1999 |
| JP | 2001-270859 | 10/2001 |
| JP | 2003-238795 | 8/2003 |
| JP | 2004-35591 | 2/2004 |
| JP | 2005-122147 A | 5/2005 |
| JP | 2006-525152 A | 11/2006 |
| JP | 2008-111025 | 5/2008 |
| JP | 2009-246360 | 10/2009 |
| JP | 2009242604 | 10/2009 |
| JP | 2009-256575 A | 11/2009 |
| JP | 2010-023234 A | 2/2010 |
| JP | 2010-121013 A | 3/2010 |
| JP | 2010-111846 A | 5/2010 |
| JP | 2010-215902 | 9/2010 |
| JP | 2011-079926 | 4/2011 |
| JP | 2011-079926 A | 4/2011 |
| JP | 2013-035275 A | 2/2013 |
| JP | 2015-530427 A | 10/2015 |
| JP | 2015-532663 A | 12/2015 |
| KR | 2009-0113576 | 11/2009 |
| KR | 2011-0001334 | 1/2011 |
| WO | WO 2000-26973 | 5/2000 |
| WO | WO 2001-98393 | 12/2001 |
| WO | WO 2002-102812 | 12/2002 |
| WO | WO 2006/109496 A1 | 10/2006 |
| WO | WO 2006/132180 A | 12/2006 |
| WO | WO 2008-122292 | 10/2008 |
| WO | WO 2009-126115 | 10/2009 |
| WO | WO 2010/0044321 | 4/2010 |
| WO | WO 2010-056559 | 12/2010 |
| WO | WO 2011/0086958 | 7/2011 |
| WO | WO 2011/093286 A1 | 8/2011 |
| WO | WO 2011/129413 | 10/2011 |
| WO | WO 2012/003198 A2 | 1/2012 |
| WO | WO 2012-003416 | 1/2012 |
| WO | WO 2012074030 A1 | 6/2012 |
| WO | WO 2012-106184 | 8/2012 |
| WO | WO 2014-025383 | 2/2014 |
| WO | WO 2014-025384 | 2/2014 |
| WO | WO 2014-025386 | 2/2014 |
| WO | WO 2014-025387 | 2/2014 |

OTHER PUBLICATIONS

Affinito, "Vacuum Deposited Polymer/Metal Multilayer Films for Optical Application", Thin Solid Films, 1995, vol. 270, pp. 43-48.

Ling, "Synthesis and Characterization of new monomers and Polymers Containing Hindered Piperidine Groups", Journal of macromolecular Science, Part A: Pure and Applied Chemistry, 1998, vol. A35, No. 7&8, pp. 1327-1336.

Ling, "Synthesis and Polymerization of New Methacryloyl Ureas Carrying a Hindered Piperidine and a Hydroxyl Group", Journal of Macromolecular Science Part A: Pure and Applied Chemistry, 2001, vol. A38, No. 2, pp. 137-158.

Plueddemann, "New Coupling Agents for improved Corrosion Resistant Composites", Polymer-Plastics Technology and Engineering, Sep./Dec. 1986, pp. 223-231.

Shaw, "A New Vapor Deposition Process for Coating Paper and Polymer Webs", Technical paper Presented at The Sixth International Vacuum Web Coating Conference in Reno, Oct. 28, 1992, pp. 18-24.

Shaw, RadTec' 96 North America UV/EB Conference Proceedings, "Use of Evaporated Acrylate Coatings to Smooth the Surface of Polyester and Polypropylene Film Substrates", 701-707 (1996).

Shaw, "Use of Vapor Deposited Acrylate Coatings to Improve the Barrier Properties of Metallized Film", Society of Vacuum Coaters 37th Annual Technical Conference Proceedings, 1994, pp. 240-247.

Shaw, "A New High Speed Process for Vapor Depositing Acrylate Thin Films: An Update", Society of Vacuum Coaters 36th Annual Technical Conference Proceedings, 1993, pp. 348-351.

Swanson, "Measurement of Web Curl", Applied Web Handling Conference 2006, 2006, 30 pages.

International Search Report for PCT International Application No. PCT/US2013/028508 dated Jun. 26, 2013, 4 pages.

Saunders and Frisch, "Polyurethanes: Chemistry and Technology" 1963 (Part I) and 1964 (Part II), Interscience Publishers, New York.

A. Matei; Functionalized ormosil scaffolds processed by direct laser polymerization for application in tissue engineering; Applied Surface Science, Oct. 26, 2012; vol. 278, p. 357-361.

Photopolymerization experiments and properties of some urehtane/urea methacrylates tested in dental composites, retrieved Jul. 25, 2017.

DIURETHANE (METH)ACRYLATE-SILANE COMPOSITIONS AND ARTICLES INCLUDING THE SAME

CROSS REFERENCE TO RELATED APPLICATIONS

This application claims the benefit of U.S. Provisional Application Nos. 61/681,003; 61/681,008; 61/681,023; 61/681,051; and 61/680,995, all filed on Aug. 8, 2012, the disclosures of which are incorporated by reference herein in their entireties.

FIELD

The present disclosure relates to the preparation of diurethane (meth)acrylate-silane compounds and their use in preparing composite barrier assemblies. More particularly, the disclosure relates to vapor-deposited protective (co)polymer layers including the reaction product of at least one diurethane (meth)acrylate-silane precursor compound, used in multilayer composite barrier assemblies in articles and barrier films.

BACKGROUND

Inorganic or hybrid inorganic/organic layers have been used in thin films for electrical, packaging and decorative applications. These layers can provide desired properties such as mechanical strength, thermal resistance, chemical resistance, abrasion resistance, moisture barriers, and oxygen barriers. Highly transparent multilayer barrier coatings have also been developed to protect sensitive materials from damage due to water vapor. The water sensitive materials can be electronic components such as organic, inorganic, and hybrid organic/inorganic semiconductor devices. The multilayer barrier coatings can be deposited directly on the sensitive material, or can be deposited on a flexible transparent substrate such as a (co)polymer film.

Multilayer barrier coatings can be prepared by a variety of production methods. These methods include liquid coating techniques such as solution coating, roll coating, dip coating, spray coating, spin coating; and dry coating techniques such as Chemical Vapor Deposition (CVD), Plasma Enhanced Chemical Vapor Deposition (PECVD), sputtering and vacuum processes for thermal evaporation of solid materials. One approach for multilayer barrier coatings has been to produce multilayer oxide coatings, such as aluminum oxide or silicon oxide, interspersed with thin (co)polymer film protective layers. Each oxide/(co)polymer film pair is often referred to as a "dyad", and the alternating oxide/(co)polymer multilayer construction can contain several dyads to provide adequate protection from moisture and oxygen. Examples of such transparent multilayer barrier coatings and processes can be found, for example, in U.S. Pat. No. 5,440,446 (Shaw et al.); U.S. Pat. No. 5,877,895 (Shaw et al.); U.S. Pat. No. 6,010,751 (Shaw et al.); U.S. Pat. No. 7,018,713 (Padiyath et al.); and U.S. Pat. No. 6,413,645 (Graff et al.).

SUMMARY

In one aspect, the present disclosure features compositions of matter including at least one diurethane (meth)acrylate-silane compound of the formula $R_A$—NH—C(O)—O—C($R^{12}R^{13}$)—C($R^{14}R^{15}$)—[C($R^{16}R^{17}$)]—O—C(O)—N($R^5$)—$R_S$. $R_A$ is a (meth)acryl group containing group of the formula $R^{11}$-(A)$_n$, wherein $R^{11}$ is a polyvalent alkylene, arylene, alkarylene, or aralkylene group, said alkylene, arylene, alkarylene, or aralkylene groups optionally containing one or more catenary oxygen atoms; A is a (meth)acryl group comprising the formula $X^2$—C(O)—C($R^3$)=$CH_2$, further wherein $X^2$ is —O, —S, or —N$R^3$, $R^3$ is independently H, or $C_1$-$C_4$, and n=1 to 5. In addition, each $R^{12}$, $R^{13}$, $R^{14}$, $R^{15}$, $R^{16}$, and $R^{17}$ is independently H, a linear, branched or cyclic alkyl group of 1 to 6 carbon atoms, optionally including 1 to 3 catenary oxygen, sulfur, or nitrogen atoms, and optionally substituted with one or more hydroxyl groups. Furthermore, $R_S$ is a silane containing group of the formula —$R^1$—[Si($Y_p$)($R^2$)$_{3-p}$]$_q$, wherein $R^1$ is a polyvalent alkylene, arylene, alkarylene, or aralkylene group, said alkylene, arylene, alkarylene, or aralkylene group, optionally containing one or more catenary oxygen atoms; Y is a hydrolysable group, $R^2$ is a monovalent alkyl or aryl group, p is 1, 2, or 3, and q is independently 1 to 5. $R^5$ is H, $C_1$ to $C_6$ alkyl, $C_1$ to $C_6$ cycloalkyl, or $R_S$; and a is 0, 1, or 2.

In any of the foregoing embodiments, each hydrolysable group Y is independently selected from an alkoxy group, an acetate group, an aryloxy group, and a halogen. In some particular exemplary embodiments of the foregoing, at least some of the hydrolysable groups Y are alkoxy groups.

In another aspect, the present disclosure describes articles including a composite barrier assembly further including a substrate selected from a (co)polymeric film or an electronic device, the electronic device further including an organic light emitting device (OLED), an electrophoretic light emitting device, a liquid crystal display, a thin film transistor, a photovoltaic device, or a combination thereof; a base (co)polymer layer on a major surface of the substrate; an oxide layer on the base (co)polymer layer; and a protective (co)polymer layer on the oxide layer. The protective (co)polymer layer includes the reaction product of at least one of the foregoing diurethane (meth)acrylate-silane precursor compounds of the formula $R_A$—NH—C(O)—O—C($R^{12}R^{13}$)—C($R^{14}R^{15}$)—[C($R^{16}R^{17}$)]$_a$—O—C(O)—N($R^5$)—$R_S$, as described above. The protective (co)polymer layer includes the reaction product of at least one of the foregoing diurethane (meth)acrylate-silane precursor compounds of the formula $R_A$—NH—C(O)—O—C($R^{12}R^{13}$)—C($R^{14}R^{15}$)—[C($R^{16}R^{17}$)]$_a$—O—C(O)—N($R^5$)—$R_S$, as described above.

In certain presently preferred exemplary embodiments of the foregoing articles, the substrate is a (co)polymeric film. In some exemplary embodiments of any of the foregoing articles, the substrate is a flexible transparent (co)polymeric film, optionally wherein the substrate comprises polyethylene terephthalate (PET), polyethylene napthalate (PEN), heat stabilized PET, heat stabilized PEN, polyoxymethylene, polyvinylnaphthalene, polyetheretherketone, a fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof. In other exemplary embodiments of any of the foregoing composite films, the base (co)polymer layer includes a (meth)acrylate smoothing layer.

In any of the foregoing articles, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

In additional exemplary embodiments of any of the foregoing articles, the article further includes a multiplicity of alternating layers of the oxide layer and the protective (co)polymer layer on the base (co)polymer layer.

In further exemplary embodiments of any of the foregoing articles, the oxide layer includes at least one oxide, nitride, carbide or boride of atomic elements selected from Groups IIA, IIIA, IVA, VA, VIA, VIIA, IB, or IIB, metals of Groups IIIB, IVB, or VB, rare-earth metals, or a combination or mixture thereof. In some exemplary embodiments of any of the foregoing composite films, the composite film further includes an oxide layer applied to the protective (co)polymer layer, optionally wherein the oxide layer includes silicon aluminum oxide.

In a further aspect, the disclosure describes methods of using a composite film as described above in an article selected from a photovoltaic device, a solid state lighting device, a display device, and combinations thereof. Exemplary solid state lighting devices include semiconductor light-emitting diodes (SLEDs, more commonly known as LEDs), organic light-emitting diodes (OLEDs), or polymer light-emitting diodes (PLEDs). Exemplary display devices include liquid crystal displays, OLED displays, and quantum dot displays.

In another aspect, the disclosure describes a process including: (a) applying a base (co)polymer layer to a major surface of a substrate, (b) applying an oxide layer on the base (co)polymer layer, and (c) depositing on the oxide layer a protective (co)polymer layer, wherein the protective (co) polymer layer includes a (co)polymer formed as the reaction product of at least one of the foregoing diurethane (meth) acrylate-silane precursor compound of the formula $R_A$—NH—C(O)—O—C($R^{12}R^{13}$)—C($R^{14}R^{15}$)—[C ($R^{16}R^{17}$)]$_a$—O—C(O)—N($R^5$)—$R_S$, as described above. The substrate is selected from a (co)polymeric film or an electronic device, the electronic device further including an organic light emitting device (OLED), an electrophoretic light emitting device, a liquid crystal display, a thin film transistor, a photovoltaic device, or a combination thereof.

In some exemplary embodiments of the process, the at least one diurethane (meth)acrylate-silane precursor compound undergoes a chemical reaction to form the protective (co)polymer layer at least in part on the oxide layer. Optionally, the chemical reaction is selected from a free radical polymerization reaction, and a hydrolysis reaction.

In any of the foregoing processes, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

In some particular exemplary embodiments of any of the foregoing processes, step (a) includes (i) evaporating a base (co)polymer precursor, (ii) condensing the evaporated base (co)polymer precursor onto the substrate, and (iii) curing the evaporated base (co)polymer precursor to form the base (co)polymer layer. In certain such exemplary embodiments, the base (co)polymer precursor includes a (meth)acrylate monomer.

In certain particular exemplary embodiments of any of the foregoing processes, step (b) includes depositing an oxide onto the base (co)polymer layer to form the oxide layer. Depositing is achieved using sputter deposition, reactive sputtering, chemical vapor deposition, or a combination thereof. In some particular exemplary embodiments of any of the foregoing processes, step (b) includes applying a layer of an inorganic silicon aluminum oxide to the base (co) polymer layer. In further exemplary embodiments of any of the foregoing processes, the process further includes sequentially repeating steps (b) and (c) to form a multiplicity of alternating layers of the protective (co)polymer layer and the oxide layer on the base (co)polymer layer.

In additional exemplary embodiments of any of the foregoing processes, step (c) further includes at least one of co-evaporating the at least one diurethane (meth)acrylate-silane precursor compound with a (meth)acrylate compound from a liquid mixture, or sequentially evaporating the at least one diurethane (meth)acrylate-silane precursor compound and a (meth)acrylate compound from separate liquid sources. Optionally, the liquid mixture includes no more than about 10 wt. % of the diurethane (meth)acrylate-silane precursor compound. In further exemplary embodiments of such processes, step (c) further includes at least one of co-condensing the diurethane (meth)acrylate-silane precursor compound with the (meth)acrylate compound onto the oxide layer, or sequentially condensing the diurethane (meth)acrylate-silane precursor compound and the (meth) acrylate compound on the oxide layer.

In further exemplary embodiments of any of the foregoing processes, reacting the diurethane (meth)acrylate-silane precursor compound with the (meth)acrylate compound to form a protective (co)polymer layer on the oxide layer occurs at least in part on the oxide layer.

Some exemplary embodiments of the present disclosure provide composite barrier assemblies, articles or barrier films which exhibit improved moisture resistance when used in moisture exposure applications. Exemplary embodiments of the disclosure can enable the formation of barrier assemblies, articles or barrier films that exhibit superior mechanical properties such as elasticity and flexibility yet still have low oxygen or water vapor transmission rates.

Exemplary embodiments of barrier assemblies or barrier films according to the present disclosure are preferably transmissive to both visible and infrared light. Exemplary embodiments of barrier assemblies or barrier films according to the present disclosure are also typically flexible. Exemplary embodiments of barrier assemblies or barrier films according to the present disclosure generally do not exhibit delamination or curl that can arise from thermal stresses or shrinkage in a multilayer structure. The properties of exemplary embodiments of barrier assemblies or barrier films disclosed herein typically are maintained even after high temperature and humidity aging.

Various aspects and advantages of exemplary embodiments of the present disclosure have been summarized. The above Summary is not intended to describe each illustrated embodiment or every implementation of the present invention. Further features and advantages are disclosed in the embodiments that follow. The Drawings and the Detailed Description that follow more particularly exemplify certain preferred embodiments using the principles disclosed herein.

BRIEF DESCRIPTION OF THE DRAWINGS

The accompanying drawings are incorporated in and constitute a part of this specification and, together with the description, explain the advantages and principles of exemplary embodiments of the present disclosure.

Like reference numerals in the drawings indicate like elements. The drawings herein are not drawn to scale, and in the drawings, the illustrated elements are sized to emphasize selected features.

DETAILED DESCRIPTION

Glossary

Figure 1:
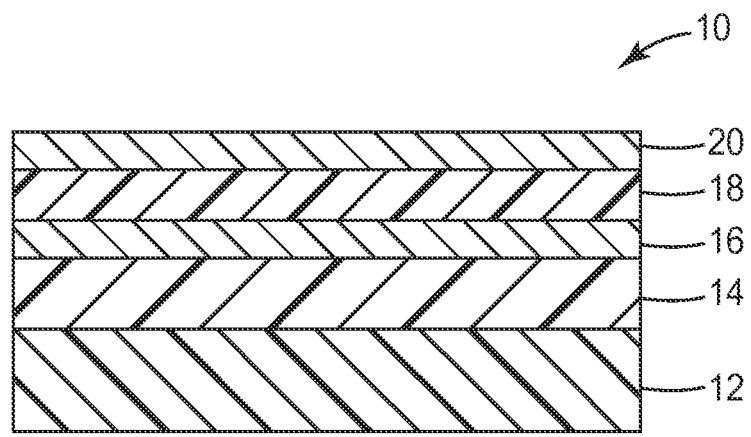
FIG. 1 is a diagram illustrating an exemplary moisture-resistant barrier assembly in an article or film having a vapor-deposited adhesion-promoting coating according to an exemplary embodiment of the present disclosure.

Certain terms are used throughout the description and the claims that, while for the most part are well known, may require some explanation. It should understood that, as used herein, The words "a", "an", and "the" are used interchangeably with "at least one" to mean one or more of the elements being described.

By using words of orientation such as "atop", "on", "covering", "uppermost", "underlying" and the like for the location of various elements in the disclosed coated articles, we refer to the relative position of an element with respect to a horizontally-disposed, upwardly-facing substrate. It is not intended that the substrate or articles should have any particular orientation in space during or after manufacture.

By using the term "overcoated" to describe the position of a layer with respect to a substrate or other element of a barrier assembly in an article or film of the disclosure, we refer to the layer as being atop the substrate or other element, but not necessarily contiguous to either the substrate or the other element.

By using the term "separated by" to describe the position of a (co)polymer layer with respect to two inorganic barrier layers, we refer to the (co)polymer layer as being between the inorganic barrier layers but not necessarily contiguous to either inorganic barrier layer.

The terms "barrier assembly," "barrier film" or "barrier layer" refers to an assembly, film or layer which is designed to be impervious to vapor, gas or aroma migration. Exemplary gases and vapors that may be excluded include oxygen and/or water vapor.

The term "(meth)acrylate" with respect to a monomer, oligomer or compound means a vinyl-functional alkyl ester formed as the reaction product of an alcohol with an acrylic or a methacrylic acid.

The term "polymer" or "(co)polymer" includes homopolymers and copolymers, as well as homopolymers or copolymers that may be formed in a miscible blend, e.g., by coextrusion or by reaction, including, e.g., transesterification. The term "copolymer" includes both random and block copolymers.

The term "cure" refers to a process that causes a chemical change, e.g., a reaction via consumption of water, to solidify a film layer or increase its viscosity.

The term "cross-linked" (co)polymer refers to a (co) polymer whose (co)polymer chains are joined together by covalent chemical bonds, usually via cross-linking molecules or groups, to form a network (co)polymer. A cross-linked (co)polymer is generally characterized by insolubility, but may be swellable in the presence of an appropriate solvent.

The term "cured (co)polymer" includes both cross-linked and uncross-linked (co)polymers.

The term "$T_g$" refer to the glass transition temperature of a cured (co)polymer when evaluated in bulk rather than in a thin film form. In instances where a (co)polymer can only be examined in thin film form, the bulk form $T_g$ can usually be estimated with reasonable accuracy. Bulk form $T_g$ values usually are determined by evaluating the rate of heat flow vs. temperature using differential scanning calorimetry (DSC) to determine the onset of segmental mobility for the (co) polymer and the inflection point (usually a second-order transition) at which the (co)polymer can be said to change from a glassy to a rubbery state. Bulk form $T_g$ values can also be estimated using a dynamic mechanical thermal analysis (DMTA) technique, which measures the change in the modulus of the (co)polymer as a function of temperature and frequency of vibration.

By using the term "visible light-transmissive" support, layer, assembly or device, we mean that the support, layer, assembly or device has an average transmission over the visible portion of the spectrum, $T_{vis}$, of at least about 20%, measured along the normal axis.

The term "metal" includes a pure metal (i.e. a metal in elemental form such as, for example silver, gold, platinum, and the like) or a metal alloy.

The term "vapor coating" or "vapor depositing" means applying a coating to a substrate surface from a vapor phase, for example, by evaporating and subsequently depositing onto the substrate surface a precursor material to the coating or the coating material itself. Exemplary vapor coating processes include, for example, physical vapor deposition (PVD), chemical vapor deposition (CVD), and combinations thereof.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Identification of a Problem to be Solved

Flexible barrier coatings or films are desirable for electronic devices whose components are sensitive to the ingress of water vapor. A multilayer barrier coating or film may provide advantages over glass as it is flexible, light-weight, durable, and enables low cost continuous roll-to-roll processing.

Each of the known methods for producing a multilayer barrier coating or film has limitations. Chemical deposition methods (CVD and PECVD) form vaporized metal alkoxide precursors that undergo a reaction, when adsorbed on a substrate, to form inorganic coatings. These processes are generally limited to low deposition rates (and consequently low line speeds), and make inefficient use of the alkoxide precursor (much of the alkoxide vapor is not incorporated into the coating). The CVD process also requires high substrate temperatures, often in the range of 300-500° C., which may not be suitable for (co)polymer substrates.

Vacuum processes such as thermal evaporation of solid materials (e.g., resistive heating or e-beam heating) also provide low metal oxide deposition rates. Thermal evaporation is difficult to scale up for roll wide web applications requiring very uniform coatings (e.g., optical coatings) and can require substrate heating to obtain quality coatings. Additionally, evaporation/sublimation processes can require ion-assist, which is generally limited to small areas, to improve the coating quality.

Sputtering has also been used to form metal oxide layers. While the deposition energy of the sputter process used for forming the barrier oxide layer is generally high, the energy involved in depositing the (meth)acrylate layers is generally low. As a result the (meth)acrylate layer typically does not have good adhesive properties with the layer below it, for example, an inorganic barrier oxide sub-layer. To increase the adhesion level of the protective (meth)acrylate layer to the barrier oxide, a thin sputtered layer of silicon sub-oxide is known to be useful in the art. If the silicon sub oxide layer is not included in the stack, the protective (meth)acrylate layer has poor initial adhesion to the barrier oxide. The silicon sub oxide layer sputter process must be carried out with precise power and gas flow settings to maintain adhesion performance. This deposition process has historically been susceptible to noise resulting in varied and low adhesion of the protective (meth)acrylate layer. It is therefore desirable to eliminate the need for a silicon sub oxide layer in the final barrier construct for increased adhesion robustness and reduction of process complexity.

Even when the "as deposited" adhesion of the standard barrier stack is initially acceptable, the sub oxide and protective (meth)acrylate layer has demonstrated weakness when exposed to accelerated aging conditions of 85° C./85% relative humidity (RH). This inter-layer weakness can result in premature delamination of the composite film from the devices it is intended to protect. It is desirable that the multi-layer construction improves upon and maintains initial adhesion levels when aged in 85° C. and 85% RH.

One solution to this problem is to use what is referred to as a "tie" layer of particular elements such chromium, zirconium, titanium, silicon and the like, which are often sputter deposited as a mono- or thin-layer of the material either as the element or in the presence of small amount of oxygen. The tie layer element can then form chemical bonds to both the substrate layer, an oxide, and the capping layer, a (co)polymer.

Tie layers are generally used in the vacuum coating industry to achieve adhesion between layers of differing materials. The process used to deposit the layers often requires fine tuning to achieve the right layer concentration of tie layer atoms. The deposition can be affected by slight variations in the vacuum coating process such as fluctuation in vacuum pressure, out-gassing, and cross contamination from other processes resulting in variation of adhesion levels in the product. In addition, tie layers often do not retain their initial adhesion levels after exposure to water vapor. A more robust solution for adhesion improvement in composite films is desirable.

Discovery of a Solution to the Problem

We have surprisingly discovered that a composite film comprising a protective (co)polymer layer comprising the reaction product of at least one diurethane (meth)acrylate-silane precursor compound as described further below, improves the adhesion and moisture barrier performance of a multilayer composite barrier assembly in an article or film. These multilayer composite barrier assemblies in articles or films have a number of applications in the photovoltaic, display, lighting, and electronic device markets as flexible replacements for glass encapsulating materials.

In exemplary embodiments of the present disclosure, the desired technical effects and solution to the technical problem to obtain improved multilayer composite barrier assemblies in articles or barrier films were obtained by chemically modifying the compositions used in the process for applying (e.g. by vapor coating) a protective (co)polymer layer to a multilayer composite barrier assembly in an article or film to achieve, in some exemplary embodiments:

1) a robust chemical bond with an inorganic oxide surface,
2) a robust chemical bond to the (meth)acrylate coating through (co)polymerization, and
3) the maintenance of some of the physical properties of the modified molecules (e.g. boiling point, vapor pressure, and the like) such that they can be co-evaporated with a bulk (meth)acrylate material.

Multilayer Composite Barrier Assemblies or Films

In exemplary embodiments, the disclosure describes a multilayer composite barrier assembly in an article or film comprising a substrate, an oxide layer on the base (co)polymer layer; and a protective (co)polymer layer on the oxide layer, the protective (co)polymer layer comprising the reaction product of at least one foregoing diurethane (meth)acrylate-silane precursor compounds of the formula $R_A$—NH—C(O)—C($R^{12}R^{13}$)—C($R^{14}R^{15}$)—[C($R^{16}R^{17}$)]$_a$—O—C(O)—N($R^5$)—$R_S$, as described further below. The substrate is selected from a (co)polymeric film or an electronic device, the electronic device further including an organic light emitting device (OLED), an electrophoretic light emitting device, a liquid crystal display, a thin film transistor, a photovoltaic device, or a combination thereof.

As further explained below, diurethane (meth)acrylate-silane precursor compounds according to the present disclosure can be prepared in two steps. In the first step, a primary or secondary aminosilane is reacted with a cyclic carbonate to yield a hydroxyalkylene-carbamoyl-alkylene-alkoxysilanes referred to as a "hydroxycarbamoylsilane"); and reacting this hydroxycarbamoylsilane with a (meth)acrylated material having isocyanate functionality, either neat or in a solvent, and optionally with a catalyst, such as a tin compound, to accelerate the reaction to provide the diurethane (meth)acrylate-silane compositions of the present disclosure.

An optional inorganic layer, which preferably is an oxide layer, can be applied over the protective (co)polymer layer. Presently preferred inorganic layers comprise at least one of silicon aluminum oxide or indium tin oxide.

Turning to the drawings, FIG. 1 is a diagram of a barrier assembly in an article or film 10 having a moisture resistant coating comprising a single dyad. Film 10 includes layers arranged in the following order: a substrate 12; a base (co)polymer layer 14; an oxide layer 16; a protective (co)polymer layer 18; and an optional oxide layer 20. Oxide layer 16 and protective (co)polymer layer 18 together form a dyad and, although only one dyad is shown, film 10 can include additional dyads of alternating oxide layer 16 and protective (co)polymer layer 18 between substrate 10 and the uppermost dyad.

In certain exemplary embodiments, the barrier assembly in an article or film comprises a plurality of alternating layers of the oxide layer and the protective (co)polymer layer on the base (co)polymer layer. The oxide layer and protective (co)polymer layer together form a "dyad", and in one exemplary embodiment, the barrier assembly in an article or film can include more than one dyad, forming a multilayer barrier assembly in an article or film. Each of the oxide layers and/or protective (co)polymer layers in the multilayer barrier assembly in an article or film (i.e. including more than one dyad) can be the same or different. An optional inorganic layer, which preferably is an oxide layer, can be applied over the plurality of alternating layers or dyads.

In some exemplary embodiments, protective (co)polymer layer 18 comprising the reaction product of at least one of the foregoing diurethane (meth)acrylate-silane precursor compounds improves the moisture resistance of film 10 and the peel strength adhesion of protective (co)polymer layer 18 to the underlying oxide layer, leading to improved adhesion and delamination resistance within the further barrier stack layers, as explained further below. Presently preferred materials for use in the barrier assembly in an article or film 10 are also identified further below, and in the Examples.

Protective (Co)Polymer Layers

The present disclosure describes protective (co)polymer layers used in composite barrier assemblies in articles and films (i.e. barrier films) useful in reducing oxygen and/or water vapor barrier transmission when used as packaging materials, for example, to package electronic devices. Each protective (co)polymer layer includes in its manufacture at least one composition of matter described herein as a diurethane (meth)acrylate-silane precursor compound, the reaction product thereof forms a (co)polymer, as described further below.

Thus, in some exemplary embodiments, the present disclosure describes a barrier assembly in an article or film including a substrate, a base (co)polymer layer on a major surface of the substrate, an oxide layer on the base (co)polymer layer, and a protective (co)polymer layer on the oxide layer. The protective (co)polymer layer includes the reaction product of at least one of the foregoing diurethane (meth)acrylate-silane precursor compounds of the formula $R_A$—NH—C(O)—O—C($R^{12}R^{13}$)—C($R^{14}R^{15}$)—[C($R^{16}R^{17}$)]$_a$—O—C(O)—N($R^5$)—$R_S$, as described further below.

In any of the foregoing articles, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

Composite Barrier Assembly or Barrier Film Materials

The present disclosure describes protective (co)polymer layers comprising the reaction product of at least one diurethane (meth)acrylate-silane precursor compound having the general formula $R_A$—NH—C(O)—N($R^4$)—$R^{11}$—[O—C(O)NH—$R_S$]$_n$, or $R_S$—NH—C(O)—N($R^4$)—$R^{11}$—[O—C(O)NH—$R_A$]$_n$, as described further below. Among other things, (co)polymer layers comprising such reaction product(s) of at least one diurethane (meth)acrylate-silane precursor compound are useful for improving the interlayer adhesion of composite barrier assemblies used in articles or barrier films.

Diurethane (Meth)acrylate Silane Precursor Compounds

The present disclosure also describes new compositions of matter comprising at least one diurethane (meth)acrylate-silane precursor compound of the formula $R_A$—NH—C(O)—O—C($R^{12}R^{13}$)—C($R^{14}R^{15}$)—[C($R^{16}R^{17}$)]$_a$—O—C(O)—N($R^5$)—$R_S$. $R_A$ is a (meth)acryl group containing group of the formula $R^{11}$-(A)$_n$, wherein $R^{11}$ is a polyvalent alkylene, arylene, alkarylene, or aralkylene group, said alkylene, arylene, alkarylene, or aralkylene groups optionally containing one or more catenary oxygen atoms; A is a (meth)acryl group comprising the formula $X^2$—C(O)—C($R^3$)=CH$_2$, further wherein $X^2$ is —O, —S, or —N$R^3$, $R^3$ is independently H, or $C_1$-$C_4$, and n=1 to 5. In addition, each $R^{12}$, $R^{13}$, $R^{14}$, $R^{15}$, $R^{16}$, and $R^{17}$ is independently H, a linear, branched or cyclic alkyl group of 1 to 6 carbon atoms, optionally including 1 to 3 catenary oxygen, sulfur, or nitrogen atoms, and optionally substituted with one or more hydroxyl groups. Furthermore, $R_S$ is a silane containing group of the formula —$R^1$—[Si(Y$_p$)($R^2$)$_{3-p}$]$_q$, wherein $R^1$ is a polyvalent alkylene, arylene, alkarylene, or aralkylene group, said alkylene, arylene, alkarylene, or aralkylene group, optionally containing one or more catenary oxygen atoms; Y is a hydrolysable group, $R^2$ is a monovalent alkyl or aryl group, p is 1, 2, or 3, and q is independently 1 to 5. $R^5$ is H, $C_1$ to $C_6$ alkyl, $C_1$ to $C_6$ cycloalkyl, or $R_S$; and a is 0, 1, or 2.

In any of the foregoing embodiments, each hydrolysable group Y is independently selected from an alkoxy group, an acetate group, an aryloxy group, and a halogen. In some particular exemplary presently preferred embodiments, at least some of the hydrolysable groups Y are alkoxy groups.

As further explained below, diurethane (meth)acrylate-silanes according to the present disclosure can be prepared in two steps. In the first step, a primary or secondary aminosilane is reacted with a cyclic carbonate to yield a hydroxyalkylene-carbamoylalkylene-alkoxysilanes referred to as a "hydroxycarbamoylsilane." The following equation is illustrative:

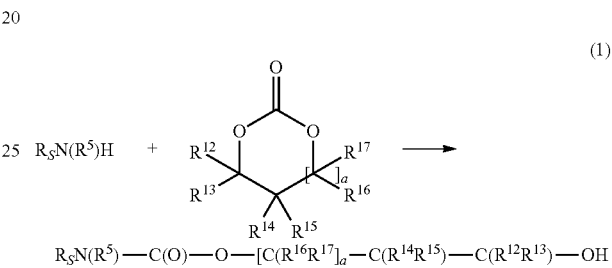

(1)

This hydroxycarbamoylsilane is then reacted with a (meth)acrylated material having isocyanate functionality, either neat or in a solvent, and optionally with a catalyst, such as a tin compound, to accelerate the reaction to provide the diurethane (meth)acrylate-silane compositions of the present disclosure.

Some suitable (meth)acrylated materials having mono-isocyanate functionality include 3-isocyanatoethyl methacrylate, 3-isocyanatoethyl methacrylate, and 1,1-bis(acryloyloxymethyl)ethyl isocyanate.

Aminosilanes suitable for use in connection with the present invention may be primary or secondary. Some primary aminosilanes useful in the practice of this invention are described in U.S. Pat. No. 4,378,250 (Treadway et al.) and include aminoethyltriethoxysilane, β-aminoethyltrimethoxysilane, β-aminoethyltriethoxysilane, β-aminoethyltributoxysilane, β-aminoethyltripropoxysilane, α-aminoethyltrimethoxysilane, α-aminoethyltriethoxysilane, γ-aminopropyltrimethoxy-silane, γ-aminopropyltriethoxysilane, γ-aminopropyltributoxysilane, γ-aminopropyltripropoxysilane, β-aminopropyltrimethoxysilane, β-aminopropyltriethoxysilane, β-aminopropyltripropoxysilane, β-aminopropyltributoxysilane, α-aminopropyltrimethoxysilane, α-aminopropyltriethoxysilane, α-aminopropyltributoxysilane, and α-aminopropyltripropoxysilane.

Some secondary aminosilanes useful in the practice of the invention include N-methyl aminopropyltrimethoxysilane, N-methyl aminopropyltriethoxysilane, bis(propyl-3-trimethoxysilane)amine, bis(propyl-3-triethoxysilane)amine, N-butyl aminopropyltrimethoxysilane, N-butyl aminopropyltriethoxysilane, N-cyclohexyl-aminopropyltrimethoxysilane, N-cyclohexyl aminomethyltrimethoxysilane, N-cyclohexyl aminomethyltriethoxysilane, and N-cyclohexyl aminomethyldiethoxy-monomethylsilane.

In some exemplary embodiments, it will be advantageous to select a silane such as a triethoxysilane which will undergo less exchange with the alcohol that is formed. It has been observed that trimethoxysilanes will often undergo the alcohol-trialkoxysilane exchange to a greater extent. Two currently preferred aminosilanes are 3-aminopropyltriethoxysilane (γ-aminopropyltriethoxysilane), and bis(propyl-3-triethoxysilane)amine.

Cyclic alkylene carbonates useful in making the hydroxycarbamoylsilanes include ethylene carbonate, and propylene carbonate (4-methyl-1,3-dioxolan-2-one) among others. When the cyclic carbonate is not symmetrical, a mixture of two regioisomers will usually result. For example, the reaction of aminopropyltriethoxysilane with propylene carbonate, followed by reaction with isocyanatoethyl methacrylate provides two products as regioisomers:

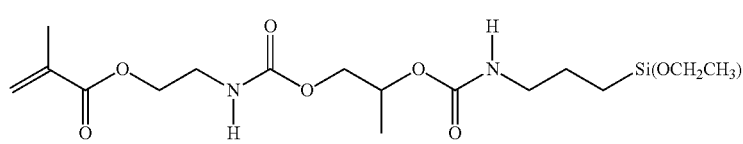

(a)

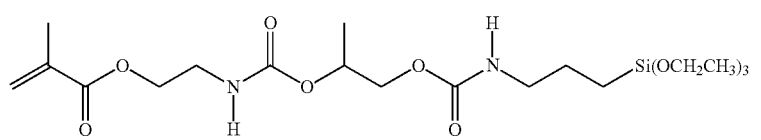

(b)

which can be represented as a single formula:

(c)

Other details about the formation of the hydroxycarbamoylsilanes may be found in U.S. Pat. No. 5,866,651.

While not intending to be bound by any particular theory, we currently believe that the reaction products of the first step, i.e. the materials of the formula $R_A$—NH—C(O)—O—$C(R^{12}R^{13})$—$C(R^{14}R^{15})$—$[C(R^{16}R^{17})]_a$—O—C(O)—N($R^5$)—$R_S$, appear to be the result of reacting each hydroxyl group of a diol selectively with a different isocyanate, one hydroxyl group reacting with an isocyanate compound having silane functionality and one hydroxyl group reacting with an isocyanate compound having acrylate functionality. A diol if reacted simultaneously or sequentially with two different isocyanate materials, one with silane functionality and one with (meth)acrylate functionality, would result in a three component mixture of diurethane compounds respectively, with 1) only acrylate groups, 2) only silane groups, along with the desired 3) acrylate and silane groups.

Using the two step sequence method of 1) reacting a primary or secondary aminosilane with a cyclic carbonate to yield a hydroxycarbamoylsilane followed by 2) reacting the hydroxycarbamoylsilane with (meth)acrylated material having isocyanate functionality cleanly produces a diurethane material with silane and (meth)acrylate functionality. Thus the material consists of materials of the formula $R_A$—NH—C(O)—O—$C(R^{12}R^{13})$—$C(R^{14}R^{15})$—$[C(R^{16}R^{17})]_a$—O—C(O)—N($R^5$)—$R_S$ without significant amounts of silane only or acrylate only material.

Additional information about the preparation of urethanes can be found in "Polyurethanes: Chemistry and Technology," Saunders and Frisch, Interscience Publishers (New York, 1963 (Part I) and 1964 (Part II).

The molecular weights of the diurethane (meth)acrylate-silane coupling agents are in the range where sufficient vapor pressure at vacuum process conditions is effective to carry out evaporation and then subsequent condensation to a thin liquid film. The molecular weights are preferably less than about 2,000 Da, more preferably less than 1,000 Da, even more preferably less than 500 Da.

Preferably, the diurethane (meth)acrylate-silane coupling agent is present at no more than 20% by weight (% wt.) of the vapor coated mixture; more preferably no more than 19%, 18%, 17%, 16%, 15%, 14%, 13%, 12%, 11%, and even more preferably 10%, 9%, 8%, 7%, 6%, 5%, 4%, 3%, 2% or even 1% wt. of the vapor deposited mixture.

Substrates

The substrate 12 is selected from a (co)polymeric film or an electronic device, the electronic device further including an organic light emitting device (OLED), an electrophoretic light emitting device, a liquid crystal display, a thin film transistor, a photovoltaic device, or a combination thereof.

Typically, the electronic device substrate is a moisture sensitive electronic device. The moisture sensitive electronic device can be, for example, an organic, inorganic, or hybrid organic/inorganic semiconductor device including, for example, a photovoltaic device such as a copper indium gallium (di)selenide (CIGS) solar cell; a display device such as an organic light emitting display (OLED), electrochromic display, electrophoretic display, or a liquid crystal display (LCD) such as a quantum dot LCD display; an OLED or other electroluminescent solid state lighting device, or combinations thereof and the like.

In some exemplary embodiments, substrate 12 can be a flexible, visible light-transmissive substrate, such as a flexible light transmissive (co)polymeric film. In one presently preferred exemplary embodiment, the substrates are substantially transparent, and can have a visible light transmission of at least about 50%, 60%, 70%, 80%, 90% or even up to about 100% at 550 nm.

Exemplary flexible light-transmissive substrates include thermoplastic (co)polymeric films including, for example, polyesters, polyacrylates (e.g., polymethyl methacrylate), polycarbonates, polypropylenes, high or low density polyethylenes, polysulfones, polyether sulfones, polyurethanes, polyamides, polyvinyl butyral, polyvinyl chloride, fluoro(co)polymers (e.g., polyvinylidene difluoride and polytetrafluoroethylene), polyethylene sulfide, and thermoset films such as epoxies, cellulose derivatives, polyimide, polyimide benzoxazole and polybenzoxazole.

Presently preferred (co)polymeric films comprise polyethylene terephthalate (PET), polyethylene napthalate (PEN), heat stabilized PET, heat stabilized PEN, polyoxymethylene, polyvinylnaphthalene, polyetheretherketone, fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof.

In some exemplary embodiments, the substrate can also be a multilayer optical film ("MOF"), such as those described in U.S. Patent Application Publication No. US 2004/0032658 A1. In one exemplary embodiment, the films can be prepared on a substrate including PET.

The (co)polymeric film can be heat-stabilized, using heat setting, annealing under tension, or other techniques that will discourage shrinkage up to at least the heat stabilization temperature when the (co)polymeric film is not constrained.

The substrate may have a variety of thicknesses, e.g., about 0.01 to about 1 mm. The substrate may however be considerably thicker, for example, when a self-supporting article is desired. Such articles can conveniently also be made by laminating or otherwise joining a disclosed film made using a flexible substrate to a thicker, inflexible or less flexible supplemental support.

Base (Co)Polymer Layer

Returning to FIG. 1, the base (co)polymer layer 14 can include any (co)polymer suitable for deposition in a thin film. In one aspect, for example, the base (co)polymer layer 14 can be formed from various precursors, for example, (meth)acrylate monomers and/or oligomers that include acrylates or methacrylates such as urethane acrylates, isobornyl acrylate, dipentaerythritol pentaacrylates, epoxy acrylates, epoxy acrylates blended with styrene, di-trimethylolpropane tetraacrylates, diethylene glycol diacrylates, 1,3-butylene glycol diacrylate, pentaacrylate esters, pentaerythritol tetraacrylates, pentaerythritol triacrylates, ethoxylated (3) trimethylolpropane triacrylates, ethoxylated (3) trimethylolpropane triacrylates, alkoxylated trifunctional acrylate esters, dipropylene glycol diacrylates, neopentyl glycol diacrylates, ethoxylated (4) bisphenol a dimethacrylates, cyclohexane dimethanol diacrylate esters, isobornyl methacrylate, cyclic diacrylates and tris(2-hydroxy ethyl) isocyanurate triacrylate, acrylates of the foregoing methacrylates and methacrylates of the foregoing acrylates. Preferably, the base (co)polymer precursor comprises a (meth) acrylate monomer.

The base (co)polymer layer 14 can be formed by applying a layer of a monomer or oligomer to the substrate and crosslinking the layer to form the (co)polymer in situ, e.g., by flash evaporation and vapor deposition of a radiation-crosslinkable monomer, followed by crosslinking using, for example, an electron beam apparatus, UV light source, electrical discharge apparatus or other suitable device. Coating efficiency can be improved by cooling the substrate.

The monomer or oligomer can also be applied to the substrate 12 using conventional coating methods such as roll coating (e.g., gravure roll coating) or spray coating (e.g., electrostatic spray coating), then crosslinked as set out above. The base (co)polymer layer 14 can also be formed by applying a layer containing an oligomer or (co)polymer in solvent and drying the thus-applied layer to remove the solvent. Plasma Enhanced Chemical Vapor Deposition (PECVD) may also be employed in some cases.

Most preferably, the base (co)polymer layer 14 is formed by flash evaporation and vapor deposition followed by crosslinking in situ, e.g., as described in U.S. Pat. No. 4,696,719 (Bischoff), U.S. Pat. No. 4,722,515 (Ham), U.S. Pat. No. 4,842,893 (Yializis et al.), U.S. Pat. No. 4,954,371 (Yializis), U.S. Pat. No. 5,018,048 (Shaw et al.), U.S. Pat. No. 5,032,461 (Shaw et al.), U.S. Pat. No. 5,097,800 (Shaw et al.), U.S. Pat. No. 5,125,138 (Shaw et al.), U.S. Pat. No. 5,440,446 (Shaw et al.), U.S. Pat. No. 5,547,908 (Furuzawa et al.), U.S. Pat. No. 6,045,864 (Lyons et al.), U.S. Pat. No. 6,231,939 (Shaw et al. and U.S. Pat. No. 6,214,422 (Yializis); in PCT International Publication No. WO 00/26973 (Delta V Technologies, Inc.); in D. G. Shaw and M. G. Langlois, "A New Vapor Deposition Process for Coating Paper and (co)polymer Webs", 6th International Vacuum Coating Conference (1992); in D. G. Shaw and M. G. Langlois, "A New High Speed Process for Vapor Depositing Acrylate Thin Films: An Update", Society of Vacuum Coaters 36th Annual Technical Conference Proceedings (1993); in D. G. Shaw and M. G. Langlois, "Use of Vapor Deposited Acrylate Coatings to Improve the Barrier Properties of Metallized Film", Society of Vacuum Coaters 37th Annual Technical Conference Proceedings (1994); in D. G. Shaw, M. Roehrig, M. G. Langlois and C. Sheehan, "Use of Evaporated Acrylate Coatings to Smooth the Surface of Polyester and Polypropylene Film Substrates", RadTech (1996); in J. Affinito, P. Martin, M. Gross, C. Coronado and E. Greenwell, "Vacuum Deposited Polymer/Metal Multilayer Films for Optical Application", Thin Solid Films 270, 43-48 (1995); and in J. D. Affinito, M. E. Gross, C. A. Coronado, G. L. Graff, E. N. Greenwell and P. M. Martin, "Polymer-Oxide Transparent Barrier Layers", Society of Vacuum Coaters 39th Annual Technical Conference Proceedings (1996).

In some exemplary embodiments, the smoothness and continuity of the base (co)polymer layer 14 (and also each oxide layer 16 and protective (co)polymer layer 18) and its adhesion to the underlying substrate or layer may be enhanced by appropriate pretreatment. Examples of a suitable pretreatment regimen include an electrical discharge in the presence of a suitable reactive or non-reactive atmosphere (e.g., plasma, glow discharge, corona discharge, dielectric barrier discharge or atmospheric pressure discharge); chemical pretreatment or flame pretreatment. These pretreatments help make the surface of the underlying layer more receptive to formation of the subsequently applied (co)polymeric (or inorganic) layer. Plasma pretreatment can be particularly useful.

In some exemplary embodiments, a separate adhesion promotion layer which may have a different composition than the base (co)polymer layer 14 may also be used atop the substrate or an underlying layer to improve adhesion. The adhesion promotion layer can be, for example, a separate (co)polymeric layer or a metal-containing layer such as a layer of metal, metal oxide, metal nitride or metal oxynitride. The adhesion promotion layer may have a thickness of a few nm (e.g., 1 or 2 nm) to about 50 nm, and can be thicker if desired.

The desired chemical composition and thickness of the base (co)polymer layer will depend in part on the nature and surface topography of the substrate. The thickness preferably is sufficient to provide a smooth, defect-free surface to which the subsequent oxide layer can be applied. For example, the base (co)polymer layer may have a thickness of a few nm (e.g., 2 or 3 nm) to about 5 micrometers, and can be thicker if desired.

In another aspect, the barrier assembly includes a substrate selected from a (co)polymer film and a moisture sensitive device, and the barrier layers are disposed on or adjacent to the substrate. As described further below, the barrier assembly can be deposited directly on a (co)polymer film substrate, or a substrate that includes a moisture sensitive device, a process often referred to as direct deposition or direct encapsulation. Exemplary direct deposition processes and barrier assemblies or described in U.S. Pat. No. 5,654,084 (Affinito); U.S. Pat. No. 6,522,067 (Graff et al.); U.S. Pat. No. 6,548,912 (Graff et al.); U.S. Pat. No. 6,573,652 (Graff et al.); and U.S. Pat. No. 6,835,950 (Brown et al.).

In some exemplary embodiments, flexible electronic devices can be encapsulated directly with the methods described herein. For example, the devices can be attached to a flexible carrier substrate, and a mask can be deposited to protect electrical connections from the inorganic layer(s), (co)polymer layer(s), or other layer(s)s during their deposition. The inorganic layer(s), (co)polymeric layer(s), and other layer(s) making up the multilayer barrier assembly can be deposited as described elsewhere in this disclosure, and the mask can then be removed, exposing the electrical connections.

In one exemplary direct deposition or direct encapsulation embodiment, the moisture sensitive device is a moisture sensitive electronic device. The moisture sensitive electronic device can be, for example, an organic, inorganic, or hybrid organic/inorganic semiconductor device including, for example, a photovoltaic device such as a copper indium gallium (di)selenide (CIGS) solar cell; a display device such as an organic light emitting display (OLED), electrochromic display, electrophoretic display, or a liquid crystal display (LCD) such as a quantum dot LCD display; an OLED or other electroluminescent solid state lighting device, or combinations thereof and the like.

Examples of suitable processes for making a multilayer barrier assembly and suitable transparent multilayer barrier coatings can be found, for example, in U.S. Pat. No. 5,440,446 (Shaw et al.); U.S. Pat. No. 5,877,895 (Shaw et al.); U.S. Pat. No. 6,010,751 (Shaw et al.); and U.S. Pat. No. 7,018,713 (Padiyath et al.). In one presently preferred embodiment, the barrier assembly in an article or film can be fabricated by deposition of the various layers onto the substrate, in a roll-to-roll vacuum chamber similar to the system described in U.S. Pat. No. 5,440,446 (Shaw et al.) and U.S. Pat. No. 7,018,713 (Padiyath, et al.).

It is presently preferred that the base polymer layer 14 is formed by flash evaporation and vapor deposition followed by crosslinking in situ, e.g., as described in U.S. Pat. No. 4,696,719 (Bischoff), U.S. Pat. No. 4,722,515 (Ham), U.S. Pat. No. 4,842,893 (Yializis et al.), U.S. Pat. No. 4,954,371 (Yializis), U.S. Pat. No. 5,018,048 (Shaw et al.), U.S. Pat. No. 5,032,461 (Shaw et al.), U.S. Pat. No. 5,097,800 (Shaw et al.), U.S. Pat. No. 5,125,138 (Shaw et al.), U.S. Pat. No. 5,440,446 (Shaw et al.), U.S. Pat. No. 5,547,908 (Furuzawa et al.), U.S. Pat. No. 6,045,864 (Lyons et al.), U.S. Pat. No. 6,231,939 (Shaw et al. and U.S. Pat. No. 6,214,422 (Yializis); and in PCT International Publication No. WO 00/26973 (Delta V Technologies, Inc.).

Oxide Layers

The improved barrier assembly in an article or film includes at least one oxide layer 16. The oxide layer preferably comprises at least one inorganic material. Suitable inorganic materials include oxides, nitrides, carbides or borides of different atomic elements. Presently preferred inorganic materials included in the oxide layer comprise oxides, nitrides, carbides or borides of atomic elements from Groups HA, IIIA, IVA, VA, VIA, VIIA, IB, or IIB, metals of Groups IIIB, IVB, or VB, rare-earth metals, or combinations thereof. In some particular exemplary embodiments, an inorganic layer, more preferably an inorganic oxide layer, may be applied to the uppermost protective (co)polymer layer. Preferably, the oxide layer comprises silicon aluminum oxide or indium tin oxide.

In some exemplary embodiments, the composition of the oxide layer may change in the thickness direction of the layer, i.e. a gradient composition. In such exemplary embodiments, the oxide layer preferably includes at least two inorganic materials, and the ratio of the two inorganic materials changes throughout the thickness of the oxide layer. The ratio of two inorganic materials refers to the relative proportions of each of the inorganic materials. The ratio can be, for example, a mass ratio, a volume ratio, a concentration ratio, a molar ratio, a surface area ratio, or an atomic ratio.

The resulting gradient oxide layer is an improvement over homogeneous, single component layers. Additional benefits in barrier and optical properties can also be realized when combined with thin, vacuum deposited protective (co)polymer layers. A multilayer gradient inorganic-(co)polymer barrier stack can be made to enhance optical properties as well as barrier properties.

The barrier assembly in an article or film can be fabricated by deposition of the various layers onto the substrate, in a roll-to-roll vacuum chamber similar to the system described in U.S. Pat. No. 5,440,446 (Shaw et al.) and U.S. Pat. No. 7,018,713 (Padiyath, et al.). The deposition of the layers can be in-line, and in a single pass through the system. In some cases, the barrier assembly in an article or film can pass through the system several times, to form a multilayer barrier assembly in an article or film having several dyads.

The first and second inorganic materials can be oxides, nitrides, carbides or borides of metal or nonmetal atomic elements, or combinations of metal or nonmetal atomic elements. By "metal or nonmetal" atomic elements is meant atomic elements selected from the periodic table Groups HA, IIIA, IVA, VA, VIA, VIIA, IB, or IIB, metals of Groups IIIB, IVB, or VB, rare-earth metals, or combinations thereof. Suitable inorganic materials include, for example, metal oxides, metal nitrides, metal carbides, metal oxynitrides, metal oxyborides, and combinations thereof, e.g., silicon oxides such as silica, aluminum oxides such as alumina, titanium oxides such as titania, indium oxides, tin oxides, indium tin oxide ("ITO"), tantalum oxide, zirconium oxide, niobium oxide, aluminum nitride, silicon nitride, boron nitride, aluminum oxynitride, silicon oxynitride, boron oxynitride, zirconium oxyboride, titanium oxyboride, and combinations thereof. ITO is an example of a special class of ceramic materials that can become electrically conducting with the proper selection of the relative proportions of each elemental constituent. Silicon-aluminum oxide and indium tin oxide are presently preferred inorganic materials forming the oxide layer 16.

For purposes of clarity, the oxide layer 16 described in the following discussion is directed toward a composition of oxides; however, it is to be understood that the composition can include any of the oxides, nitrides, carbides, borides, oxynitrides, oxyborides and the like described above.

In one embodiment of the oxide layer 16, the first inorganic material is silicon oxide, and the second inorganic material is aluminum oxide. In this embodiment, the atomic ratio of silicon to aluminum changes throughout the thickness of the oxide layer, e.g., there is more silicon than aluminum near a first surface of the oxide layer, gradually becoming more aluminum than silicon as the distance from the first surface increases. In one embodiment, the atomic ratio of silicon to aluminum can change monotonically as the distance from the first surface increases, i.e., the ratio either increases or decreases as the distance from the first surface increases, but the ratio does not both increase and decrease as the distance from the first surface increases. In another embodiment, the ratio does not increase or decrease monotonically, i.e. the ratio can increase in a first portion, and decrease in a second portion, as the distance from the first surface increases. In this embodiment, there can be several increases and decreases in the ratio as the distance from the first surface increases, and the ratio is non-monotonic. A change in the inorganic oxide concentration from one oxide species to another throughout the thickness of the oxide layer 16 results in improved barrier performance, as measured by water vapor transmission rate.

In addition to improved barrier properties, the gradient composition can be made to exhibit other unique optical properties while retaining improved barrier properties. The gradient change in composition of the layer produces corresponding change in refractive index through the layer. The materials can be chosen such that the refractive index can change from high to low, or vice versa. For example, going from a high refractive index to a low refractive index can allow light traveling in one direction to easily pass through the layer, while light travelling in the opposite direction may be reflected by the layer. The refractive index change can be used to design layers to enhance light extraction from a light emitting device being protected by the layer. The refractive index change can instead be used to pass light through the layer and into a light harvesting device such as a solar cell. Other optical constructions, such as band pass filters, can also be incorporated into the layer while retaining improved barrier properties.

In order to promote silane bonding to the oxide surface, it may be desirable to form hydroxyl silanol (Si—OH) groups on a freshly sputter deposited silicon dioxide ($SiO_2$) layer. The amount of water vapor present in a multi-process vacuum chamber can be controlled sufficiently to promote the formation of Si—OH groups in high enough surface concentration to provide increased bonding sites. With residual gas monitoring and the use of water vapor sources the amount of water vapor in a vacuum chamber can be controlled to ensure adequate generation of Si—OH groups.

Process for Making Articles Including Barrier Assemblies or Barrier Films

In other exemplary embodiments, the disclosure describes a process, e.g. for making a barrier film on a (co)polymer film substrate or for making an article by depositing a multilayer composite barrier assembly on an electronic device substrate, the process including: (a) applying a base (co)polymer layer to a major surface of a substrate, (b) applying an oxide layer on the base (co)polymer layer, and (c) depositing on the oxide layer a protective (co)polymer layer, wherein the protective (co)polymer layer includes a (co)polymer formed as the reaction product of at least one of the foregoing diurethane (meth)acrylate-silane precursor compound of the formula $R_A$—NH—C(O)—O—C ($R^{12}R^{13}$)—C($R^{14}R^{15}$)—[C($R^{16}R^{17}$)$_a$—O—C(O)—N($R^5$)—$R_S$, as described above. The substrate is selected from a (co)polymeric film or an electronic device, the electronic device further including an organic light emitting device (OLED), an electrophoretic light emitting device, a liquid crystal display, a thin film transistor, a photovoltaic device, or a combination thereof.

In some exemplary embodiments of the process, the at least one diurethane (meth)acrylate-silane precursor compound undergoes a chemical reaction to form the protective (co)polymer layer at least in part on the oxide layer. Optionally, the chemical reaction is selected from a free radical polymerization reaction, and a hydrolysis reaction.

In any of the foregoing articles, each hydrolysable group Y is independently selected from an alkoxy group, an acetate group, an aryloxy group, and a halogen. In some particular exemplary embodiments of the foregoing articles, at least some of the hydrolysable groups Y are alkoxy.

In some particular exemplary embodiments of any of the foregoing processes, step (a) comprises: (i) evaporating a base (co)polymer precursor, (ii) condensing the evaporated base (co)polymer precursor onto the substrate, and (iii) curing the evaporated base (co)polymer precursor to form the base (co)polymer layer. In certain such exemplary embodiments, the base (co)polymer precursor includes a (meth)acrylate monomer.

In certain particular exemplary embodiments of any of the foregoing processes, step (b) comprises depositing an oxide onto the base (co)polymer layer to form the oxide layer. Depositing is achieved using sputter deposition, reactive sputtering, chemical vapor deposition, or a combination thereof. In some particular exemplary embodiments of any of the foregoing processes, step (b) comprises applying a layer of an inorganic silicon aluminum oxide to the base (co)polymer layer. In further exemplary embodiments of any of the foregoing processes, the process further comprises sequentially repeating steps (b) and (c) to form a multiplicity of alternating layers of the protective (co)polymer layer and the oxide layer on the base (co)polymer layer.

In additional exemplary embodiments of any of the foregoing processes, step (c) further comprises at least one of co-evaporating the at least one diurethane (meth)acrylate-silane precursor compound with a (meth)acrylate compound from a liquid mixture, or sequentially evaporating the at least one diurethane (meth)acrylate-silane precursor compound and a (meth)acrylate compound from separate liquid sources. Optionally, the liquid mixture comprises no more than about 10 wt. % of the diurethane (meth)acrylate-silane precursor compound. In further exemplary embodiments of such processes, step (c) further comprises at least one of co-condensing the diurethane (meth)acrylate-silane precursor compound with the (meth)acrylate compound onto the oxide layer, or sequentially condensing the diurethane (meth)acrylate-silane precursor compound and the (meth) acrylate compound on the oxide layer.

In further exemplary embodiments of any of the foregoing processes, reacting the diurethane (meth)acrylate-silane precursor compound with the (meth)acrylate compound to form a protective (co)polymer layer on the oxide layer occurs at least in part on the oxide layer.

In another presently preferred exemplary embodiment, the disclosure describes a process for making a barrier film, the process comprising: (a) vapor depositing and curing a base (co)polymer layer onto a major surface of a (co) polymer film substrate; (b) vapor depositing an oxide layer on the base (co)polymer layer; and (c) vapor depositing and curing onto the oxide layer a protective (co)polymer layer, the protective (co)polymer layer comprising a (co)polymer formed as the reaction product of at least one of the foregoing diurethane (meth)acrylate-silane precursor compounds of the formula $R_A$—NH—C(O)—O—C($R^{12}R^{13}$)—C($R^{14}R^{15}$)—[C($R^{16}R^{17}$)]$_a$—O—C(O)—N($R^5$)—$R_S$, as previously described.

The vapor deposition process is generally limited to compositions that are pumpable (liquid-phase with an acceptable viscosity); that can be atomized (form small droplets of liquid), flash evaporated (high enough vapor pressure under vacuum conditions), condensable (vapor pressure, molecular weight), and can be cross-linked in vacuum (molecular weight range, reactivity, functionality).

Figure 2:
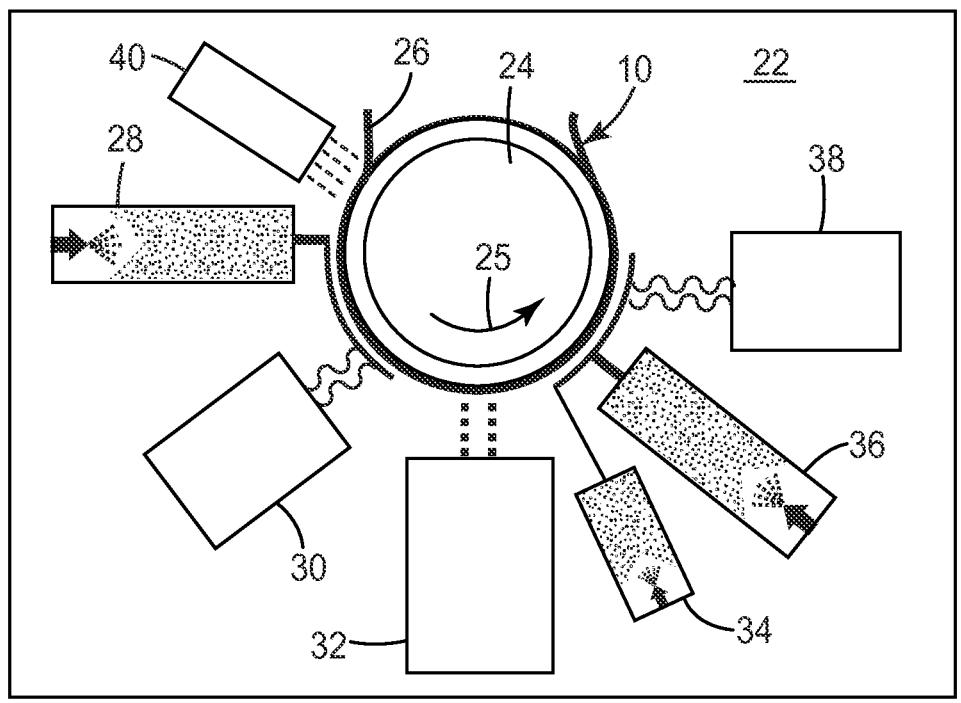
FIG. 2 is a diagram illustrating an exemplary process and apparatus for making a composite film according to an exemplary embodiment of the present disclosure.

FIG. 2 is a diagram of a system 22, illustrating a process for making barrier assembly in an article or film 10. System 22 is contained within an inert environment and includes a chilled drum 24 for receiving and moving the substrate 12 (FIG. 1), as represented by a film 26, thereby providing a moving web on which to form the barrier layers. Preferably, an optional nitrogen plasma treatment unit 40 may be used to plasma treat or prime film 26 in order to improve adhesion of the base (co)polymer layer 14 (FIG. 1) to substrate 12 (FIG. 1). An evaporator 28 applies a base (co)polymer precursor, which is cured by curing unit 30 to form base (co)polymer layer 14 (FIG. 1) as drum 24 advances the film 26 in a direction shown by arrow 25. An oxide sputter unit 32 applies an oxide to form layer 16 (FIG. 1) as drum 24 advances film 26.

For additional alternating oxide layers 16 and protective (co)polymer layers 18, drum 24 can rotate in a reverse direction opposite arrow 25 and then advance film 26 again to apply the additional alternating base (co)polymer and oxide layers, and that sub-process can be repeated for as many alternating layers as desired or needed. Once the base (co)polymer and oxide are complete, drum 24 further advances the film, and evaporator 36 deposits on oxide layer 16, the urea (multi)-(meth)acrylate (multi)-silane compound (as described above), which is reacted or cured to form protective (co)polymer layer 18 (FIG. 1). In certain presently preferred embodiments, reacting the urea (multi)-(meth)acrylate (multi)-silane compound to form a protective (co)polymer layer 18 on the oxide layer 16 occurs at least in part on the oxide layer 16.

Optional evaporator 34 may be used additionally to provide other co-reactants or co-monomers (e.g., additional protective (co)polymer compounds) which may be useful in forming the protective (co)polymer layer 18 (FIG. 1). For additional alternating oxide layers 16 and protective (co) polymer layers 18, drum 24 can rotate in a reverse direction opposite arrow 25 and then advance film 26 again to apply the additional alternating oxide layers 16 and protective (co)polymer layers 18, and that sub-process can be repeated for as many alternating layers or dyads as desired or needed.

The oxide layer 16 can be formed using techniques employed in the film metalizing art such as sputtering (e.g., cathode or planar magnetron sputtering), evaporation (e.g., resistive or electron beam evaporation), chemical vapor deposition, plating and the like. In one aspect, the oxide layer 16 is formed using sputtering, e.g., reactive sputtering. Enhanced barrier properties have been observed when the oxide layer is formed by a high energy deposition technique such as sputtering compared to lower energy techniques such as conventional chemical vapor deposition processes. Without being bound by theory, it is believed that the enhanced properties are due to the condensing species arriving at the substrate with greater kinetic energy as occurs in sputtering, leading to a lower void fraction as a result of compaction.

In some exemplary embodiments, the sputter deposition process can use dual targets powered by an alternating current (AC) power supply in the presence of a gaseous atmosphere having inert and reactive gasses, for example argon and oxygen, respectively. The AC power supply alternates the polarity to each of the dual targets such that for half of the AC cycle one target is the cathode and the other target is the anode. On the next cycle the polarity switches between the dual targets. This switching occurs at a set frequency, for example about 40 kHz, although other frequencies can be used. Oxygen that is introduced into the process forms oxide layers on both the substrate receiving the inorganic composition, and also on the surface of the target. The dielectric oxides can become charged during sputtering, thereby disrupting the sputter deposition process. Polarity switching can neutralize the surface material being sputtered from the targets, and can provide uniformity and better control of the deposited material.

In further exemplary embodiments, each of the targets used for dual AC sputtering can include a single metal or nonmetal element, or a mixture of metal and/or nonmetal elements. A first portion of the oxide layer closest to the moving substrate is deposited using the first set of sputtering targets. The substrate then moves proximate the second set of sputtering targets and a second portion of the oxide layer is deposited on top of the first portion using the second set of sputtering targets. The composition of the oxide layer changes in the thickness direction through the layer.

In additional exemplary embodiments, the sputter deposition process can use targets powered by direct current (DC) power supplies in the presence of a gaseous atmosphere having inert and reactive gasses, for example argon and oxygen, respectively. The DC power supplies supply power (e.g. pulsed power) to each cathode target independent of the other power supplies. In this aspect, each individual cathode target and the corresponding material can be sputtered at differing levels of power, providing additional control of composition through the layer thickness. The pulsing aspect of the DC power supplies is similar to the frequency aspect in AC sputtering, allowing control of high rate sputtering in the presence of reactive gas species such as oxygen. Pulsing DC power supplies allow control of polarity switching, can neutralize the surface material being sputtered from the targets, and can provide uniformity and better control of the deposited material.

In one particular exemplary embodiment, improved control during sputtering can be achieved by using a mixture, or atomic composition, of elements in each target, for example a target may include a mixture of aluminum and silicon. In another embodiment, the relative proportions of the elements in each of the targets can be different, to readily provide for a varying atomic ratio throughout the oxide layer. In one embodiment, for example, a first set of dual AC sputtering targets may include a 90/10 mixture of silicon and aluminum, and a second set of dual AC sputtering targets may include a 75/25 mixture of aluminum and silicon. In this embodiment, a first portion of the oxide layer can be deposited with the 90% Si/10% Al target, and a second portion can be deposited with the 75% Al/25% Si target. The resulting oxide layer has a gradient composition that changes from about 90% Si to about 25% Si (and conversely from about 10% Al to about 75% Al) through the thickness of the oxide layer.

In typical dual AC sputtering, homogeneous oxide layers are formed, and barrier performance from these homogeneous oxide layers suffer due to defects in the layer at the micro and nano-scale. One cause of these small scale defects is inherently due to the way the oxide grows into grain boundary structures, which then propagate through the thickness of the film.

Without wishing to be bound by any particular theory, it is currently believed that several effects contribute to the improved barrier properties of the gradient composition barriers described herein. One effect can be that greater densification of the mixed oxides occurs in the gradient region, and any paths that water vapor could take through the oxide are blocked by this densification. Another effect can be that by varying the composition of the oxide materials, grain boundary formation can be disrupted resulting in a microstructure of the film that also varies through the thickness of the oxide layer. Another effect can be that the concentration of one oxide gradually decreases as the other oxide concentration increases through the thickness, reducing the probability of forming small-scale defect sites. The reduction of defect sites can result in a coating having reduced transmission rates of water permeation.

In some exemplary embodiments, exemplary films can be subjected to post-treatments such as heat treatment, ultraviolet (UV) or vacuum UV (VUV) treatment, or plasma treatment. Heat treatment can be conducted by passing the film through an oven or directly heating the film in the coating apparatus, e.g., using infrared heaters or heating directly on a drum. Heat treatment may for example be performed at temperatures from about 30° C. to about 200° C., about 35° C. to about 150° C., or about 40° C. to about 70° C.

Other functional layers or coatings that can be added to the inorganic or hybrid film include an optional layer or layers to make the film more rigid. The uppermost layer of the film is optionally a suitable protective layer, such as optional inorganic layer 20. If desired, the protective layer can be applied using conventional coating methods such as roll coating (e.g., gravure roll coating) or spray coating (e.g., electrostatic spray coating), then cross-linked using, for example, UV radiation. The protective layer can also be formed by flash evaporation, vapor deposition and cross-linking of a monomer as described above. Volatilizable (meth)acrylate monomers are suitable for use in such a protective layer. In a specific embodiment, volatilizable (meth)acrylate monomers are employed.

Methods of Using Barrier Films

In a further aspect, the disclosure describes methods of using a barrier film made as described above in an article selected from a solid state lighting device, a display device, and combinations thereof. Exemplary solid state lighting devices include semiconductor light-emitting diodes (SLEDs, more commonly known as LEDs), organic light-emitting diodes (OLEDs), or polymer light-emitting diodes (PLEDs). Exemplary display devices include liquid crystal displays, OLED displays, and quantum dot displays.

Exemplary LEDs are described in U.S. Pat. No. 8,129,205. Exemplary OLEDs are described in U.S. Pat. Nos. 8,193,698 and 8,221,176. Exemplary PLEDs are described in U.S. Pat. No. 7,943,062

Unexpected Results and Advantages

Exemplary barrier assemblies in articles or films of the present disclosure have a number of applications and advantages in the display, lighting, and electronic device markets as flexible replacements for glass encapsulating materials. Thus, certain exemplary embodiments of the present disclosure provide barrier assemblies in articles or films which exhibit improved moisture resistance when used in moisture barrier applications. In some exemplary embodiments, the barrier assembly can be deposited directly on a substrate that includes a moisture sensitive device, a process often referred to as direct encapsulation.

The moisture sensitive device can be a moisture sensitive electronic device, for example, an organic, inorganic, or hybrid organic/inorganic semiconductor device including, for example, a photovoltaic device such as a CIGS; a display device such as an OLED, electrochromic, or an electrophoretic display; an OLED or other electroluminescent solid state lighting device, or others. Flexible electronic devices can be encapsulated directly with the gradient composition oxide layer. For example, the devices can be attached to a flexible carrier substrate, and a mask can be deposited to protect electrical connections from the oxide layer deposition. A base (co)polymer layer and the oxide layer can be deposited as described above, and the mask can then be removed, exposing the electrical connections.

Exemplary embodiments of the disclosed methods can enable the formation of barrier assemblies in articles or films that exhibit superior mechanical properties such as elasticity and flexibility yet still have low oxygen or water vapor transmission rates. The barrier assemblies have at least one inorganic or hybrid organic/oxide layer or can have additional inorganic or hybrid organic/oxide layers. In one embodiment, the disclosed barrier assemblies can have inorganic or hybrid organic layers alternating with organic compound, e.g., (co)polymer layers. In another embodiment, the barrier assemblies can have a film that includes an inorganic or hybrid material and an organic compound. Substrates having a barrier assembly formed using the disclosed method can have an oxygen transmission rate (OTR) less than about 1 cc/m$^2$-day, less than about 0.5 cc/m$^2$-day, or less than about 0.1 cc/m$^2$-day. Substrates having a barrier assembly formed using the disclosed method can have an water vapor transmission rate (WVTR) less than about 10 cc/m$^2$-day, less than about 5 cc/m$^2$-day, or less than about 1 cc/m$^2$-day.

Exemplary embodiments of barrier assemblies in articles and barrier films according to the present disclosure are preferably transmissive to both visible and infrared light. The term "transmissive to visible and infrared light" as used herein can mean having an average transmission over the visible and infrared portion of the spectrum of at least about 75% (in some embodiments at least about 80, 85, 90, 92, 95, 97, or 98%) measured along the normal axis. In some embodiments, the visible and infrared light-transmissive assembly has an average transmission over a range of 400 nm to 1400 nm of at least about 75% (in some embodiments at least about 80, 85, 90, 92, 95, 97, or 98%). Visible and infrared light-transmissive assemblies are those that do not interfere with absorption of visible and infrared light, for example, by photovoltaic cells. In some embodiments, the visible and infrared light-transmissive assembly has an average transmission over a range wavelengths of light that are useful to a photovoltaic cell of at least about 75% (in some embodiments at least about 80, 85, 90, 92, 95, 97, or 98%). The first and second (co)polymeric film substrates, pressure sensitive adhesive layer, and barrier film can be selected based on refractive index and thickness to enhance transmission to visible and infrared light.

Exemplary embodiments of barrier assemblies in articles and barrier films according to the present disclosure are typically flexible. The term "flexible" as used herein with respect to a barrier film refers to being capable of being formed into a roll. In some barrier film embodiments, the term "flexible" refers to being capable of being bent around a roll core with a radius of curvature of up to 7.6 centimeters (cm) (3 inches), in some embodiments up to 6.4 cm (2.5 inches), 5 cm (2 inches), 3.8 cm (1.5 inch), or 2.5 cm (1 inch). In some embodiments, the flexible assembly can be bent around a radius of curvature of at least 0.635 cm (¼ inch), 1.3 cm (½ inch) or 1.9 cm (¾ inch).

Exemplary barrier assemblies in articles and barrier films according to the present disclosure generally do not exhibit delamination or curl that can arise from thermal stresses or shrinkage in a multilayer structure. Herein, curl is measured for barrier films using a curl gauge described in "Measurement of Web Curl" by Ronald P. Swanson presented in the 2006 AWEB conference proceedings (Association of Industrial Metallizers, Coaters and Laminators, Applied Web Handling Conference Proceedings, 2006). According to this method curl can be measured to the resolution of 0.25 m$^{-1}$ curvature. In some embodiments, barrier films according to the present disclosure exhibit curls of up to 7, 6, 5, 4, or 3 m$^{-1}$. From solid mechanics, the curvature of a beam is known to be proportional to the bending moment applied to it. The magnitude of bending stress is in turn is known to be proportional to the bending moment. From these relations the curl of a sample can be used to compare the residual stress in relative terms.

Barrier films also typically exhibit high peel adhesion to EVA, and other common encapsulants for photovoltaics, cured on a substrate. The properties of the barrier films disclosed herein typically are maintained even after high temperature and humidity aging.

Exemplary embodiments of the present disclosure have been described above and are further illustrated below by way of the following Examples, which are not to be construed in any way as imposing limitations upon the scope of the present disclosure. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

EXAMPLES

The following examples are intended to illustrate exemplary embodiments within the scope of this disclosure. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Materials

The following materials, abbreviations, and trade names are used in the Examples:

90% Si/10% Al targets were obtained from Materion Advanced Chemicals, Inc. (Albuquerque, N. Mex.).

ETFE film: Ethylene-tetrafluoroethylene film available from St. Gobain Performance Plastics (Wayne, N.J.) under the trade name "NORTON® ETFE."

Table 1 lists the materials used to prepare (multi) (meth) acrylate (multi) silane compounds according to the foregoing disclosure:

TABLE 1

Materials Used in the Examples

| Material Type | Trade Name or Acronym | Description |
|---|---|---|
| (Meth)acrylated material w/ isocyanate functionality | BEI | 1,1-bis(acryloyloxymethyl) ethyl isocyanate available from CBC America Corp. (Commack, NY) |
| (Meth)acrylated material w/ isocyanate functionality | IEA | Isocyanatoethyl acrylate available from CBC America Corp. (Commack, NY) |
| (Meth)acrylated material w/ isocyanate functionality | IEM | Isocyanatoethyl methacrylate available from CBC America Corp. (Commack, NY) |
| Cyclic carbonate | PC | Propylene carbonate available from Alfa Aesar (Ward Hill, MA) |
| Cyclic carbonate | EC | Ethylene carbonate available from Sigma Aldrich (Milwaukee, WI) |
| Catalyst | DBTDL | Dibutyltin dilaurate available from Sigma Aldrich (Milwaukee, WI) |
| Solvent | MEK | Methyl ethyl ketone available from EMD Chemicals, Inc. |
| Amino-functional silane | Dynasylan AMMO | 3-Aminopropyltrimethoxysilane available from Evonik, Inc. (Piscataway, NJ) |
| Amino-functional silane | Dynasylan AMEO | 3-Aminopropyltriethoxysilane available from Evonik, Inc. (Piscataway, NJ) |
| Amino-functional silane | Dynasylan 1122 | bis-(3-triethoxysilylpropyl)amine available from Evonik, Inc. (Piscataway, NJ) |
| Amino-functional silane | — | N-methyl-3-aminopropyltrimethoxysilane available from SynQuest Labs, Inc. (Alachua, FL) |

Solvents and other reagents used were obtained from Sigma-Aldrich Chemical Company (Milwaukee, Wis.), unless otherwise specified.

Synthesis of Diurethane (Meth)Acrylate-Silane Precursor Compounds

Preparative Example 1

A 250 mL round bottom flask was charged with 23.06 g (0.2259 mol) of propylene carbonate and 102 microliters of a 10% solution of dibutyltin dilaurate (DBTDL) in methyl ethyl ketone (500 ppm DBTDL), and placed in a 55° C. oil bath. Using a pressure equalizing dropping funnel, 50.0 g (0.2259 mol) of aminopropyltriethoxysilane (Dynasylan AMEO) was added over the course of 10 min. Heating was continued for 2 hours to provide a mixture of (EtO)$_3$Si—(CH$_2$)$_3$—NH—C(O)—O—CH$_2$CH(CH$_3$)—OH and (EtO)$_3$Si—(CH$_2$)$_3$—NH—C(O)—O—CH(CH$_3$)CH$_2$—OH.

A fresh 250 ml, round bottom flask was charged with 32.27 g (0.221 mol) of isocyanatoethyl methacrylate (IEM) and 1244 microliters of a 10% solution of DBTDL in methyl ethyl ketone (1000 ppm of additional DBTDL) and placed in a 55° C. oil bath. To the flask was added 71.45 g (0.221 mol) of the mixture described above over the course of 30 min. Heating was continued for 1.5 hours of additional reaction time. A sample was then taken for fourier transform infrared (FTIR) spectroscopic analysis, with the sample showing no isocyanate peak at 2265 cm$^{-1}$:

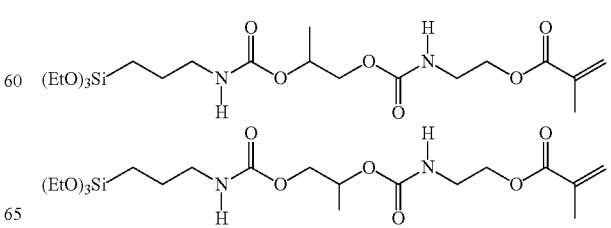

Preparative Example 2

An experiment was run similar to Preparative Example 1, except that, in the first reaction, 19.89 g (0.2259 mol) of ethylene carbonate was reacted with 50.0 g (0.2259 mol) of aminopropyltriethoxysilane (Dynasylan AMEO), and except that no DBTDL solution was added. A carbamate alcohol was formed.

A second reaction was run similar to the second reaction of Example 1 except that 67.37 g (0.2177 mol) of the carbamate alcohol was then reacted with 33.78 g (0.2177 mol) of isocyanatoethyl methacrylate (IEM) and about 1000 ppm DBTDL to provide the product:

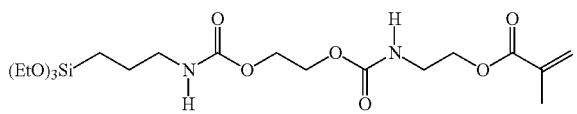

Preparative Example 3

A 250 mL round bottom flask was charged with 8.79 g (0.086 mol) of propylene carbonate and 300 ppm of DBTDL in MEK solution and placed in a 55° C. oil bath. Using a pressure equalizing dropping funnel, 19.06 g (0.086 mol) of aminopropyltriethoxysilane (Dynasylan AMEO) was added over the course of 10 min. Heating was continued for 6 hours to provide a mixture of $(EtO)_3Si-(CH_2)_3-NH-C(O)-O-CH_2CH(CH_3)-OH$ and $(EtO)_3Si-(CH_2)_3-NH-C(O)-O-CH(CH_3)CH_2-OH$.

An additional 1000 ppm DBTDL was added to the flask. Using an addition funnel, 12.15 g (0.086 mol) IEA was added to the reaction over 10 min. After 2 hours additional reaction time, FTIR analysis showed no isocyanate peak, and the product was isolated as a thick whitish paste:

Preparative Example 5

A 250 mL roundbottom equipped with overhead stirrer was charged with 23.08 g (0.226 mol) of propylene carbonate. The flask was then further charged with 430 microliters (about 5640 ppm) of DBTDL in MEK solution, and placed under dry air at 55° C. A dry dropping funnel was rinsed with aminopropyltriethoxysilane (Dynasylan AMEO) and material was allowed to drain through the funnel by gravity. The funnel was then tared and and used to charge the flask with 50.00 g (0.226 mol) of aminopropyl-trimethoxysilane, which was added to the reaction over 11 minutes. After 1 hour of total reaction time (including addition), the reaction was sampled for proton NMR analysis, whereupon it was found that the reaction was incomplete. The flask was placed in a refrigerator overnight. In the morning, the reaction was heated for 4 hours at 55° C., at which time the NMR analysis was performed again. This time the results revealed that the reaction was it was substantially complete.

About half of the product was removed from the flask, leaving 35.05 g (0.108 mol) of the propylene carbonate-aminopropyltrimethoxysilane carbamate alcohol adduct in the flask. An additional 150 microliters of DBTDL solution was added to the flask. A dry dropping funnel was rinsed with 1,1-bis(acryloyloxymethyl)ethyl isocyanate (BEI) and this material was allowed to drain through the funnel by gravity. The funnel was then tared and used to further charge the flask with 25.89 g (0.108 mol) of BEI which was added to the reaction over about 10 minutes. After 8 hours of reaction at 55° C. and standing at to room temperature for 12 hour, FTIR analysis showed no isocyanate peak, proving the product:

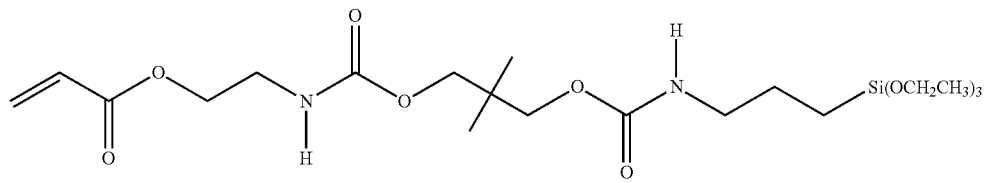

Preparative Example 4

An experiment was run similar to Preparative Example 3, except that, in the first reaction 7.82 g (0.089 mol) of ethylene carbonate was reacted with 19.65 g (0.089 mol) of aminopropyltriethoxysilane (Dynasylan AMEO) in the presence of 300 ppm DBTDL to provide a carbamate alcohol.

Similarly to Preparatory Example 3, an additional 1000 ppm DBTDL was added to the flask. Using an addition funnel, 12.53 g (0.089 mol) of IEA was added to the reaction over 10 min. The following product was obtained:

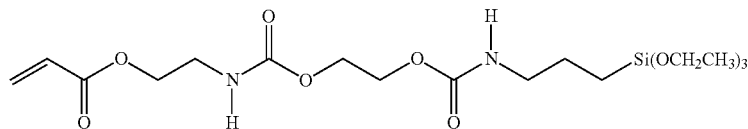

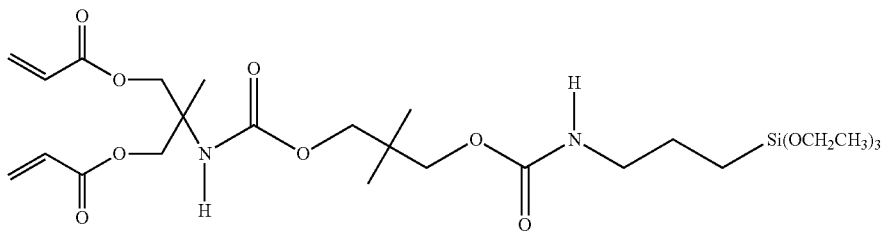

The structure indicates that the material is a mixture of products, with a methyl group located on either of the carbons between the two oxygen atoms separated by the hash mark.

Preparative Example 6

A 100 mL roundbottom equipped with overhead stirrer was charged with 8.0 g (0.078 mol) propylene carbonate and 97 microliters of a solution of DBTDL in MEK solution (providing 2353 ppm of DBTDL). The flask was placed in a 50° C. oil bath under dry air. Via an addition funnel, 33.36 g (0.078 mol) of bis(3-trimethoxysilylpropyl)amine was added over about 15 minutes, to provide a urethane alcohol disilane in the form of a yellow clear liquid.

After 3.5 hours of additional reaction time, the flask was further charged with 36 microliters of the DBTDL, and 26.02 g (0.078 mol) of IEA was added to the flask over the course of about 15 min. The temperature was reduced to 40° C. overnight, and after that time FTIR analysis showed no isocyanate peak and the product was isolated:

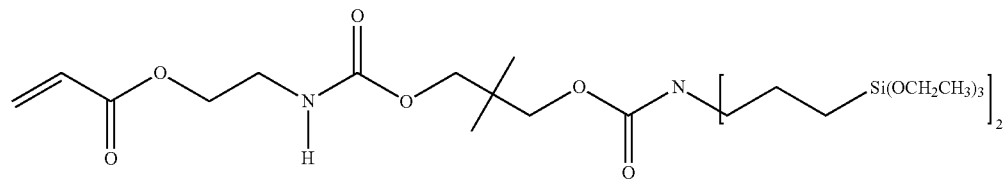

Preparative Example 7

A 100 mL roundbottom equipped with overhead stirrer was charged with 8.0 g (0.078 mol) propylene carbonate and 97 microliters of a solution of DBTDL in MEK solution (providing 2353 ppm of DBTDL). The flask was placed in a 50° C. oil bath under dry air. Via an addition funnel, 33.36 g (0.078 mol) of bis(3-trimethoxysilylpropyl)amine were reacted over about 20 hours at 40° C. to provide the same urethane alcohol disilane intermediate as in Preparative Example 6.

The flask was further charged with an additional 44 microliters of DBTDL solution, and 18.75 g (0.078 mol) of BEI was added to the flask over the course of about 10 min. After reaction for about 1 day, FTIR analysis showed no isocyanate peak and the product was isolated:

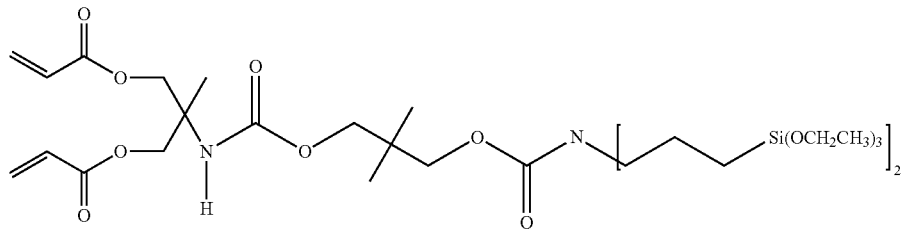

Composite Barrier Assembly and Barrier Film Preparation

Examples of multilayer composite barrier assemblies and barrier films were made on a vacuum coater similar to the coater described in U.S. Pat. No. 5,440,446 (Shaw et al.) and U.S. Pat. No. 7,018,713 (Padiyath, et al.).

Comparative Example 8 and Examples 9 through 13 below relate to forming simulated barrier modules which were subjected to under conditions designed to simulate aging in an outdoor environment and then subjected to a peel adhesion test to determine if the diurethane (meth)acrylate-silane precursor compounds of the above Preparative Examples were effective in improving peel adhesion. Some procedures common to all these Examples are presented first.

Composite films according to the examples below were laminated to a 0.05 mm thick ethylene tetrafluoroethylene (ETFE) film commercially available as NORTON® ETFE from St. Gobain Performance Plastics of Wayne, N.J., using a 0.05 mm thick pressure sensitive adhesive (PSA) commercially available as 3M OPTICALLY CLEAR ADHESIVE 8172P from 3M Company, of St. Paul, Minn. The laminated barrier sheets formed in each Example below was then placed atop a 0.14 mm thick polytetrafluoroethylene (PTFE) coated aluminum-foil commercially available commercially as 8656K61, from McMaster-Carr, Santa Fe Springs, Calif. with 13 mm wide desiccated edge tape commercially available as SOLARGAIN Edge Tape SET LP01" from Truseal Technologies Inc. of Solon, Ohio) placed around the perimeter of the foil between the barrier sheet and the PTFE.

A 0.38 mm thick encapsulant film commercially available as JURASOL from JuraFilms of Downer Grove, Ill. and an additional layer of the laminated barrier sheet were placed on the backside of the foil with the encapsulant between the barrier sheet and the foil. The multi-component constructions were vacuum laminated at 150° C. for 12 min.

Test Methods

Aging Test

Some of the laminated constructions described above were aged for 250 hrs and 500 hours in an environmental chamber set to conditions of 85° C. and 85% relative humidity.

T-Peel Adhesion Test

Unaged and aged barrier sheets were cut away from the PTFE surface and divided into 1.0 inch (25.4 mm) wide strips for adhesion testing using the ASTM D1876-08 T-peel test method. The samples were peeled by a peel tester commercially available as INISIGHT 2 SL equipped with TESTWORKS 4 software commercially available from MTS of Eden Prairie, Minn. A peel rate of 10 in/min (25.4 cm/min) was used. The reported adhesion value in Table II below is the average of four peel measurements.

Example 8 (Comparative)

This example is comparative in the sense that no coupling agents as described in Examples 1 through 7 were used. A polyetheylene terephthalate (PET) substrate film was covered with a stack of an acrylate smoothing layer, an inorganic silicon aluminum oxide (SiAlOx) barrier and an acrylate protective layer. The individual layers were formed as follows:

(Deposition of the (Meth)Acrylate Smoothing Layer)

A 305 meter long roll of 0.127 mm thick by 366 mm wide PET film commercially available XST 6642 from Dupont of Wilmington, Del. was loaded into a roll-to-roll vacuum processing chamber. The chamber was pumped down to a pressure of $1\times10^{-5}$ Torr. The web speed was maintained at 4.8 meter/min while maintaining the backside of the film in contact with a coating drum chilled to $-10°$ C. With the film in contact with the drum, the film surface was treated with a nitrogen plasma at 0.02 kW of plasma power. The film surface was then coated with tricyclodecane dimethanol diacrylate commercially available as SR-833S from Sartomer USA, LLC, Exton, Pa.). More specifically, the diacrylate was degassed under vacuum to a pressure of 20 mTorr prior to coating, loaded into a syringe pump, and pumped at a flow rate of 1.33 mL/min through an ultrasonic atomizer operated at a frequency of 60 kHz into a heated vaporization chamber maintained at 260° C. The resulting monomer vapor stream condensed onto the film surface and was electron beam crosslinked using a multi-filament electron-beam cure gun operated at 7.0 kV and 4 mA to form a 720 nm acrylate layer.

(Deposition of the Inorganic Silicon Aluminum Oxide (SiAlOx) Barrier)

Immediately after the acrylate deposition and with the film still in contact with the drum, a SiAlOx layer was sputter-deposited atop the acrylate-coated web surface. Two alternating current (AC) power supplies were used to control two pairs of cathodes; with each cathode housing two 90% Si/10% Al targets commercially available from Materion of Albuquerque, N. Mex. During sputter deposition, the voltage signal from each power supply was used as an input for a proportional-integral-differential control loop to maintain a predetermined oxygen flow to each cathode. The AC power supplies sputtered the 90% Si/10% Al targets using 5000 watts of power, with a gas mixture containing 450 sccm argon and 63 sccm oxygen at a sputter pressure of 3.5 millitorr. This provided a 30 nm thick SiAlOx layer deposited atop the acrylate discussed above.

(Deposition of the (Meth)Acrylate Protective Layer)

Immediately after the SiAlOx layer deposition and with the film still in contact with the drum, an acrylate protective layer second was coated and crosslinked on the same web generally using the same conditions as for the deposition of the smoothing layer, but with the following exceptions. The electron beam crosslinking was carried out using a multi-filament electron-beam cure gun operated at 7 kV and 5 mA. This provided a 720 nm thick acrylate layer atop Layer 2.

The resulting three layer stack on the (co)polymeric substrate exhibited an average spectral transmission $T_{vis}$ of 87%, determined by averaging the percent transmission T between 400 nm and 700 nm, measured at a 0° angle of incidence. A water vapor transmission rate (WVTR) was measured in accordance with ASTM F-1249 at 50° C. and 100% relative humidity (RH) using MOCON PERMATRAN-W® Model 700 WVTR testing system commercially available from MOCON, Inc, Minneapolis, Minn.). The result was below the 0.005 g/m²/day lower detection limit rate of the apparatus.

The resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 9

A poly(ethylene) terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 2 above was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 10

A poly(ethylene) terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 3 above was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 11

A poly(ethylene) terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 4 above was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 12

A poly(ethylene) terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 6 above was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 13

A poly(ethylene) terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 7 above was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

Example 14 (Comparative)

A poly(ethylene) terephthalate (PET) substrate film was covered with a stack of an acrylate smoothing layer, an inorganic silicon aluminum oxide (SiAlOx) barrier and an acrylate protective layer containing the disclosure molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of N-n-butyl-AZA-2,2-dimethoxysilacyclopentane (commercially available from Gelest, Morrisville, Pa., under the product code 1932.4) was used instead.

The resulting three layer stack on the (co)polymeric substrate exhibited an average spectral transmission $T_{vis}$=87% and a below the 0.005 g/m$^2$/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

TABLE 2

Test Results for Examples 8-13

| Example | T-Peel Initial (N/cm) | T-Peel After Aging 250 Hours @ 85° C./ 85% RH (N/cm) | T-Peel After Aging 1000 Hours @ 85° C./ 85% RH (N/cm) |
|---|---|---|---|
| 8 (Comparative) | 0.3 | 0.1 | 0.1 |
| 9 | 9.8 | 10.3 | 11.0 |
| 10 | 0.3 | 0.1 | 0.2 |
| 11 | 9.3 | 9.8 | — |
| 12 | 8.6 | 9.5 | 5.5 |
| 13 | 8.9 | 10.0 | 0.4 |
| 14 (Comparative) | 6.0 | 10.1 | 0.4 |

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. Furthermore, all publications, published patent applications and issued patents referenced herein are incorporated by reference in their entirety to the same extent as if each individual publication or patent was specifically and individually indicated to be incorporated by reference. Various exemplary embodiments have been described. These and other embodiments are within the scope of the following listing of disclosed embodiments and claims.

The invention claimed is:

1. A composition of matter, comprising:
   at least one diurethane (meth)acrylate-silane compound of the formula:

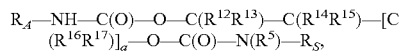

$R_A$—NH—C(O)—O—C($R^{12}R^{13}$)—C($R^{14}R^{15}$)—[C($R^{16}R^{17}$)]$_a$—O—C(O)—N($R^5$)—$R_S$, wherein:
   $R_A$ is a (meth)acryl group containing group of the formula $R^{11}$-(A)$_n$, further wherein:
   $R^{11}$ is a polyvalent alkylene, arylene, alkarylene, or aralkylene group, said alkylene, arylene, alkarylene, or aralkylene groups optionally containing one or more catenary oxygen atoms,
   A is a (meth)acryl group comprising the formula $X^2$—C(O)—C($R^3$)=CH$_2$, additionally wherein:
   $X^2$ is —O, —S, or —NR$^3$,
   $R^3$ is independently H, or $C_1$-$C_4$ alkyl, and
   n=1 to 5;
   each $R^{12}$, $R^{13}$, $R^{14}$, $R^{15}$, $R^{16}$, and $R^{17}$ is independently H, a linear, branched or cyclic alkyl group of 1 to 6 carbon atoms, optionally comprising 1 to 3 catenary oxygen, sulfur, or nitrogen atoms, and optionally substituted with one or more hydroxyl groups;
   $R_S$ is a silane containing group of the formula —$R^1$—[Si($Y_p$)($R^2$)$_{3-p}$]$_q$, wherein:
   $R^1$ is a polyvalent alkylene, arylene, alkarylene, or aralkylene group, said alkylene, arylene, alkarylene, or aralkylene group optionally containing one or more catenary oxygen atoms,
   Y is a hydrolysable group,
   $R^2$ is a monovalent alkyl or aryl group,
   p is 1, 2, or 3, and
   q is independently 1 to 5;
   $R^5$ is H, $C_1$ to $C_6$ alkyl, $C_3$ to $C_6$ cycloalkyl, or $R_S$; and
   a is 0, 1, or 2.

2. A composition of matter according to claim 1, wherein each hydrolysable group Y is independently selected from an alkoxy group, an acetate group, an aryloxy group, and a halogen.

3. A composition of matter according to claim 2, wherein at least some of the hydrolysable groups Y are alkoxy groups.

4. An article, comprising:
   a substrate selected from a (co)polymeric film or an electronic device, the electronic device further comprising an organic light emitting device (OLED), an electrophoretic light emitting device, a liquid crystal display, a thin film transistor, a photovoltaic device, or a combination thereof;
   a base (co)polymer layer on a major surface of the substrate;
   an oxide layer on the base (co)polymer layer; and
   a protective (co)polymer layer on the oxide layer, wherein the protective (co)polymer layer comprises the reaction product of at least one diurethane (meth)acrylate-silane precursor compound of the formula:

$R_A$—NH—C(O)—O—C($R^{12}R^{13}$)—C($R^{14}R^{15}$)—[C($R^{16}R^{17}$)]$_a$—O—C(O)—N($R^5$)—$R_S$, wherein:
   $R_A$ is a (meth)acryl group containing group of the formula $R^{11}$-(A)$_n$, further wherein:
   $R^{11}$ is a polyvalent alkylene, arylene, alkarylene, or aralkylene group, said alkylene, arylene, alkarylene, or aralkylene groups optionally containing one or more catenary oxygen atoms,
   A is a (meth)acryl group comprising the formula $X^2$—C(O)—C($R^3$)=CH$_2$, additionally further wherein:
   $X^2$ is —O, —S, or —NR$^3$,
   $R^3$ is independently H, or $C_1$-$C_4$ alkyl, and
   n=1 to 5;
   each $R^{12}$, $R^{13}$, $R^{14}$, $R^{15}$, $R^{16}$, and $R^{17}$ is independently H, a linear, branched or cyclic alkyl group of 1 to 6 carbon atoms optionally comprising 1 to 3 catenary oxygen, sulfur, or nitrogen atoms, and optionally substituted with one or more hydroxyl groups;
   $R_S$ is a silane containing group of the formula —$R^1$—[Si($Y_p$)($R^2$)$_{3-p}$]$_q$, wherein:
   $R^1$ is a polyvalent alkylene, arylene, alkarylene, or aralkylene group, said alkylene, arylene, alkarylene, or aralkylene group optionally containing one or more catenary oxygen atoms,
   Y is a hydrolysable group,
   $R^2$ is a monovalent alkyl or aryl group
   p is 1, 2, or 3, and
   q is independently 1 to 5;
   $R^5$ is H, $C_1$ to $C_6$ alkyl, $C_3$ to $C_6$ cycloalkyl, or $R_S$; and
   a is 0, 1, or 2.

5. The article of claim 4, wherein each hydrolysable group Y is independently selected from an alkoxy group, an acetate group, an aryloxy group, and a halogen.

6. The article of claim 5, wherein at least some of the hydrolysable groups Y are alkoxy groups.

7. The article of claim 4, further comprising a plurality of alternating layers of the oxide layer and the protective (co)polymer layer on the base (co)polymer layer.

8. The article of claim 4, wherein the substrate comprises a flexible transparent (co)polymeric film, optionally wherein the substrate comprises polyethylene terephthalate (PET), polyethylene napthalate (PEN), heat stabilized PET, heat stabilized PEN, polyoxymethylene, polyvinylnaphthalene, polyetheretherketone, fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof.

9. The article of claim 4, wherein the base (co)polymer layer comprises an acrylate smoothing layer.

10. The article of claim 4, wherein the oxide layer comprises oxides, nitrides, carbides or borides of atomic elements from Groups IIA, IIIA, IVA, VA, VIA, VIIA, IB, or IIB, metals of Groups IIIB, IVB, or VB, rare-earth metals, or combinations thereof.

11. The article of claim 4, further comprising an oxide layer applied to the protective (co)polymer layer, optionally wherein the oxide layer comprises silicon aluminum oxide.

12. An electronic device incorporating the article according to claim 4, wherein the substrate is a (co)polymer film and the electronic device is selected from a solid state lighting device, a display device, and combinations thereof.

13. A process, comprising:
(a) applying a base (co)polymer layer to a major surface of a substrate selected from a (co)polymeric film or an electronic device, the electronic device further comprising an organic light emitting device (OLED), an electrophoretic light emitting device, a liquid crystal display, a thin film transistor, a photovoltaic device, or a combination thereof;
(b) applying an oxide layer on the base (co)polymer layer; and
(c) depositing on the oxide layer a protective (co)polymer layer, wherein the protective (co)polymer layer comprises the reaction product of at least one diurethane (meth)acrylate-silane precursor compound of the formula:

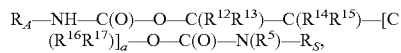

wherein:
$R_A$ is a (meth)acryl group containing group of the formula $R^{11}$-$(A)_n$, further wherein:
$R^{11}$ is a polyvalent alkylene, arylene, alkarylene, or aralkylene group, said alkylene, arylene, alkarylene, or aralkylene groups optionally containing one or more catenary oxygen atoms,
A is a (meth)acryl group comprising the formula $X^2$—C(O)—C($R^3$)=CH$_2$, additionally wherein:
$X^2$ is —O, —S, or —NR$^3$, and
$R^3$ is independently H, or $C_1$-$C_4$ alkyl, and
n=1 to 5;
each $R^{12}$, $R^{13}$, $R^{14}$, $R^{15}$, $R^{16}$, and $R^{17}$ is independently H, a linear, branched or cyclic alkyl group of 1 to 6 carbon atoms, optionally comprising 1 to 3 catenary oxygen, sulfur, or nitrogen atoms, and optionally substituted with one or more hydroxyl groups; and
$R_S$ is a silane containing group of the formula —$R^1$—[Si($Y_p$)($R^2$)$_{3-p}$]$_q$, wherein:
$R^1$ is a polyvalent alkylene, arylene, alkarylene, or aralkylene group, said alkylene, arylene, alkarylene, or aralkylene group optionally containing one or more catenary oxygen atoms,
Y is a hydrolysable group,
$R^2$ is a monovalent alkyl or aryl group;
p is 1, 2, or 3, and
q is independently 1 to 5;
$R^5$ is H, $C_1$ to $C_6$ alkyl, $C_3$ to $C_6$ cycloalkyl, or $R_S$; and
a is 0, 1, or 2.

14. The process of claim 13, wherein each hydrolysable group Y is independently selected from an alkoxy group, an acetate group, an aryloxy group, and a halogen.

15. The process of claim 13, wherein the at least one diurethane (meth)acrylate-silane precursor compound undergoes a chemical reaction to form the protective (co)polymer layer at least in part on the oxide layer, optionally wherein the chemical reaction is selected from a free radical polymerization reaction, and a hydrolysis reaction.

16. The process of claim 13, wherein step (a) comprises:
(i) evaporating the base (co)polymer precursor;
(ii) condensing the evaporated base (co)polymer precursor onto the substrate; and
(iii) curing the evaporated base (co)polymer precursor to form the base (co)polymer layer.

17. The process of claim 13, wherein step (b) comprises depositing an oxide onto the base (co)polymer layer to form the oxide layer, wherein depositing is achieved using sputter deposition, reactive sputtering, chemical vapor deposition, or a combination thereof.

18. The process of any claim 13, further comprising sequentially repeating steps (b) and (c) to form a plurality of alternating layers of the protective (co)polymer layer and the oxide layer on the base (co)polymer layer.

19. The process claim 13, wherein step (c) further comprises at least one of co-evaporating the at least one diurethane (meth)acrylate-silane precursor compound with a (meth)acrylate compound from a liquid mixture, or sequentially evaporating the at least one diurethane (meth)acrylate-silane precursor compound and a (meth)acrylate compound from separate liquid sources, optionally wherein the liquid mixture comprises no more than about 10 wt. % of the diurethane (meth)acrylate-silane precursor compound.

20. The process of claim 13, wherein step (c) further comprises at least one of co-condensing the diurethane (meth)acrylate-silane precursor compound with the (meth)acrylate compound onto the oxide layer, or sequentially condensing the diurethane (meth)acrylate-silane precursor compound and the (meth)acrylate compound on the oxide layer.

* * * * *

UNITED STATES PATENT AND TRADEMARK OFFICE
CERTIFICATE OF CORRECTION

PATENT NO. : 10,011,735 B2
APPLICATION NO. : 14/419324
DATED : July 3, 2018
INVENTOR(S) : Thomas Klun et al.

Page 1 of 2

It is certified that error appears in the above-identified patent and that said Letters Patent is hereby corrected as shown below:

In the Specification

Column 1
Line 66, Delete "-$[C(R^{16}R^{17})]$-" and insert -- -$[C(R^{16}R^{17})]_a$- --, therefor.

Column 2
Line 49, Delete "napthalate" and insert -- naphthalate --, therefor.

Column 8
Line 17, Delete "-$C(O)-C(R^{12}R^{13})$-" and insert -- -$C(O)-O-C(R^{12}R^{13})$- --, therefor.

Column 10
Line 29 (approx.), Delete "-$[C(R^{16}R^{17}]_a$-" and insert -- -$[C(R^{16}R^{17})]_a$- --, therefor.

Column 13
Line 17, Delete "napthalate" and insert -- naphthalate --, therefor.

Column 16
Line 51, Delete "HA," and insert -- IIA, --, therefor.

Column 18
Line 1, Delete "-$[C(R^{16}R^{17}]_a$-" and insert -- -$[C(R^{16}R^{17})]_a$- --, therefor.

Column 21
Line 48, After "7,943,062" insert -- . --.

Column 24
Line 47 (approx.), Delete "ml," and insert -- mL --, therefor.

Signed and Sealed this
Twenty-ninth Day of January, 2019

Andrei Iancu
*Director of the United States Patent and Trademark Office*

CERTIFICATE OF CORRECTION (continued)
U.S. Pat. No. 10,011,735 B2

Column 26
Line 11 (approx.), Delete "and and" and insert -- and --, therefor.

Column 29
Line 48, Delete "INISIGHT" and insert -- INSIGHT --, therefor.
Line 58, Delete "polyetheylene" and insert -- polyethylene --, therefor.

In the Claims

Column 35
Line 12, In Claim 8, delete "napthalate" and insert -- naphthalate --, therefor.

Column 36
Line 40 (approx.), In Claim 18, after "of" delete "any".
Line 44 (approx.), In Claim 19, after "process" insert -- of --.

UNITED STATES PATENT AND TRADEMARK OFFICE
CERTIFICATE OF CORRECTION

| | | |
|---|---|---|
| PATENT NO. | : 10,011,735 B2 | Page 1 of 1 |
| APPLICATION NO. | : 14/419324 | |
| DATED | : July 3, 2018 | |
| INVENTOR(S) | : Thomas P Klun | |

It is certified that error appears in the above-identified patent and that said Letters Patent is hereby corrected as shown below:

In the Specification

<u>Column 1</u>
Line 13, insert:
--GOVERNMENT RIGHTS
This invention was made with Government support under DE-EE0004739 awarded by DOE. The Government has certain rights in this invention.--

Signed and Sealed this
Thirty-first Day of December, 2024

Derrick Brent
*Acting Director of the United States Patent and Trademark Office*